US012690827B2

(12) United States Patent
Onishi et al.

(10) Patent No.: US 12,690,827 B2
(45) Date of Patent: Jul. 28, 2026

(54) RADIOGRAPHY METHOD, TRAINED MODEL, RADIOGRAPHY MODULE, RADIOGRAPHY PROGRAM, RADIOGRAPHY SYSTEM, AND MACHINE LEARNING METHOD

(71) Applicant: HAMAMATSU PHOTONICS K.K., Hamamatsu (JP)

(72) Inventors: Tatsuya Onishi, Hamamatsu (JP); Toshiyasu Suyama, Hamamatsu (JP)

(73) Assignee: HAMAMATSU PHOTONICS K.K., Hamamatsu (JP)

( * ) Notice: Subject to any disclaimer, the term of this patent is extended or adjusted under 35 U.S.C. 154(b) by 71 days.

(21) Appl. No.: 17/918,178

(22) PCT Filed: Apr. 14, 2021

(86) PCT No.: PCT/JP2021/015488

§ 371 (c)(1),
(2) Date: Oct. 11, 2022

(87) PCT Pub. No.: WO2021/210617

PCT Pub. Date: Oct. 21, 2021

(65) Prior Publication Data

US 2023/0125182 A1      Apr. 27, 2023

(30) Foreign Application Priority Data

Apr. 16, 2020      (JP) ................................. 2020-073576

(51) Int. Cl.
*A61B 6/00*          (2024.01)
*A61B 6/42*          (2024.01)
*G06T 5/70*          (2024.01)
(52) U.S. Cl.
CPC ................ *A61B 6/42* (2013.01); *A61B 6/482* (2013.01); *G06T 5/70* (2024.01);
(Continued)

(58) Field of Classification Search
None
See application file for complete search history.

(56) References Cited

U.S. PATENT DOCUMENTS

| 5,335,260 A | 8/1994 | Arnold |
| 5,565,678 A | 10/1996 | Manian |
| (Continued) | | |

FOREIGN PATENT DOCUMENTS

| CN | 102297873 A | 12/2011 |
| CN | 103649990 A | 3/2014 |
| (Continued) | | |

OTHER PUBLICATIONS

Sungmin Cha et al, "Fully Convolutional Pixel Adaptive Image Denoiser", arxiv.org, Cornell University Library, 201 Olin Library Cornell University Ithaca, NY 14853, Jul. 19, 2018, p. 1-p. 19, XP081114501.

(Continued)

*Primary Examiner* — Dani Fox
(74) *Attorney, Agent, or Firm* — FAEGRE DRINKER BIDDLE & REATH LLP

(57) ABSTRACT

A control device includes an input unit configured to accept an input of condition information indicating either operating conditions of a source of X-rays when the X-rays are radiated to capture an image of a target object or imaging conditions during capturing an image of the target object, a calculation unit configured to calculate average energy of the X-rays passing through the target object on the basis of the condition information, and a narrowing unit configured to narrow down candidates for a trained model from a plurality of trained models constructed through machine training in advance using image data on the basis of the average energy.

14 Claims, 17 Drawing Sheets

(52) U.S. Cl.
CPC .............. *G06T 2207/10116* (2013.01); *G06T 2207/20081* (2013.01); *G06T 2207/20182* (2013.01)

(56) References Cited

U.S. PATENT DOCUMENTS

| | | |
|---|---|---|
| 5,585,603 A | 12/1996 | Vogeley, Jr. |
| 5,687,210 A | 11/1997 | Maitrejean et al. |
| 5,917,877 A | 6/1999 | Chiabrera et al. |
| 6,173,038 B1 | 1/2001 | Siffert et al. |
| 6,198,795 B1 | 3/2001 | Naumann et al. |
| 6,201,850 B1 | 3/2001 | Heumann |
| 6,231,231 B1 | 5/2001 | Farrokhnia et al. |
| 6,269,142 B1 | 7/2001 | Smith |
| 6,315,447 B1 | 11/2001 | Nord et al. |
| 6,347,131 B1 | 2/2002 | Gusterson |
| 6,370,223 B1 | 4/2002 | Gleason et al. |
| 6,398,408 B1 | 6/2002 | Polkus |
| 6,516,045 B2 | 2/2003 | Shepherd et al. |
| 6,570,955 B1 | 5/2003 | Siffert et al. |
| 6,574,302 B2 | 6/2003 | Adriaansz |
| 6,574,303 B2 | 6/2003 | Sawada |
| 6,600,805 B2 | 7/2003 | Hansen |
| 6,632,020 B2 | 10/2003 | Kaufhold et al. |
| 6,661,868 B2 | 12/2003 | Sawada |
| 6,872,949 B2 | 3/2005 | Mizuoka et al. |
| 7,260,177 B2 | 8/2007 | Hirose |
| 7,311,440 B2 | 12/2007 | Yoon et al. |
| 7,467,892 B2 | 12/2008 | Lang et al. |
| 7,477,726 B2 | 1/2009 | Kabumoto |
| 7,570,787 B2 | 8/2009 | Hirose |
| 7,696,480 B2 | 4/2010 | Kostka et al. |
| 7,746,976 B2 | 6/2010 | Huo et al. |
| 7,980,760 B2 | 7/2011 | Kabumoto et al. |
| 7,991,110 B2 | 8/2011 | Hirose |
| 8,068,656 B2 | 11/2011 | Hirose |
| 8,077,827 B2 | 12/2011 | Perng |
| 8,223,922 B2 | 7/2012 | Suyama et al. |
| 8,280,005 B2 | 10/2012 | Suyama et al. |
| 8,858,076 B2 | 10/2014 | Quintana et al. |
| 8,873,825 B2 | 10/2014 | Mercuriev |
| 8,938,110 B2 | 1/2015 | Goshen et al. |
| 8,989,345 B2 | 3/2015 | Kim et al. |
| 9,413,995 B2 | 8/2016 | Ohguri |
| 9,547,889 B2 | 1/2017 | Goshen |
| 9,615,808 B2 | 4/2017 | Mentrup |
| 9,619,906 B2 | 4/2017 | Choi et al. |
| 9,886,765 B2 | 2/2018 | Naito |
| 9,943,282 B2 | 4/2018 | Katsumata |
| 10,010,304 B2 | 7/2018 | Morita |
| 10,242,443 B2 | 3/2019 | Hsieh et al. |
| 10,430,708 B1 | 10/2019 | Hu et al. |
| 10,803,555 B2 | 10/2020 | Song et al. |
| 10,820,197 B2 | 10/2020 | Rosenberg et al. |
| 10,824,857 B2 | 11/2020 | Flohr et al. |
| 10,832,381 B2 | 11/2020 | Strobel et al. |
| 10,888,296 B2 | 1/2021 | Ji et al. |
| 10,949,951 B2 | 3/2021 | Tang et al. |
| 10,970,887 B2 | 4/2021 | Wang et al. |
| 10,984,564 B2 | 4/2021 | Bergner |
| 11,126,914 B2 | 9/2021 | Thibault et al. |
| 11,166,694 B2 | 11/2021 | Takagi |
| 11,185,302 B2 | 11/2021 | Tsuchiya et al. |
| 11,195,277 B2 | 12/2021 | Shanbhag et al. |
| 11,244,480 B2 | 2/2022 | Teshigawara et al. |
| 11,257,196 B2 | 2/2022 | Kaneko |
| 11,324,472 B2 | 5/2022 | Hamill |
| 11,386,592 B2 | 7/2022 | Paysan et al. |
| 11,436,720 B2 | 9/2022 | Gong et al. |
| 11,501,431 B2 | 11/2022 | Xiao et al. |
| 11,517,197 B2 | 12/2022 | Zhou et al. |
| 11,574,170 B2 | 2/2023 | Isogawa et al. |
| 11,710,230 B2 | 7/2023 | Takeshima et al. |
| 11,798,159 B2 | 10/2023 | Zhou et al. |
| 11,972,559 B2 | 4/2024 | Hamauzu |
| 12,094,037 B2 | 9/2024 | Takahashi |
| 12,141,965 B2 | 11/2024 | Mao et al. |
| 12,167,926 B2 | 12/2024 | Nishii et al. |
| 12,243,127 B2 | 3/2025 | Lee et al. |
| 2005/0078802 A1 | 4/2005 | Lang et al. |
| 2011/0206177 A1 | 8/2011 | Hirasawa |
| 2012/0224760 A1 | 9/2012 | Goshen et al. |
| 2013/0051516 A1 | 2/2013 | Yang et al. |
| 2013/0071876 A1 | 3/2013 | Hao et al. |
| 2015/0342554 A1 | 12/2015 | Mentrup et al. |
| 2015/0371414 A1 | 12/2015 | Choi et al. |
| 2017/0065244 A1 | 3/2017 | Taki |
| 2018/0122094 A1 | 5/2018 | Naito |
| 2018/0349759 A1* | 12/2018 | Isogawa .................... G06T 5/60 |
| 2019/0035058 A1 | 1/2019 | Strobel et al. |
| 2019/0102621 A1 | 4/2019 | Flohr et al. |
| 2019/0108441 A1 | 4/2019 | Thibault et al. |
| 2019/0201106 A1 | 7/2019 | Siemionow et al. |
| 2019/0325621 A1 | 10/2019 | Wang et al. |
| 2019/0385345 A1 | 12/2019 | Bergner |
| 2020/0065940 A1 | 2/2020 | Tang et al. |
| 2020/0241150 A1 | 7/2020 | Ikeda et al. |
| 2020/0286214 A1 | 9/2020 | Kaneko |
| 2020/0315566 A1 | 10/2020 | Takagi |
| 2021/0059629 A1 | 3/2021 | Hamill |
| 2021/0251583 A1 | 8/2021 | Hamauza |
| 2022/0313199 A1 | 10/2022 | Nishii et al. |
| 2023/0135988 A1 | 5/2023 | Onishi et al. |
| 2023/0136930 A1 | 5/2023 | Suyama et al. |

FOREIGN PATENT DOCUMENTS

| | | |
|---|---|---|
| CN | 102577356 B | 11/2014 |
| CN | 106233127 A | 12/2016 |
| CN | 107516330 A | 12/2017 |
| CN | 107533019 A | 1/2018 |
| CN | 107595312 A | 1/2018 |
| CN | 107871332 A | 4/2018 |
| CN | 108139489 A | 6/2018 |
| CN | 108271411 A | 7/2018 |
| CN | 108926353 A | 12/2018 |
| CN | 109544477 A | 3/2019 |
| CN | 109697476 A | 4/2019 |
| CN | 109805950 A | 5/2019 |
| CN | 109983325 A | 7/2019 |
| CN | 115398215 A | 11/2022 |
| JP | 2001-099941 A | 4/2001 |
| JP | 2003-167060 A | 6/2003 |
| JP | 2006-318103 A | 11/2006 |
| JP | 2008-229161 A | 10/2008 |
| JP | 2013-512024 A | 4/2013 |
| JP | 2018-117900 A | 8/2018 |
| JP | 2018-206382 A | 12/2018 |
| JP | 6454820 B1 | 1/2019 |
| JP | 2019045235 A | 3/2019 |
| JP | 2019-068912 A | 5/2019 |
| JP | 2019-091393 A | 6/2019 |
| JP | 2019-111322 A | 7/2019 |
| JP | 2019-158663 A | 9/2019 |
| JP | 2019168360 A | 10/2019 |
| JP | 2019-202087 A | 11/2019 |
| JP | 2019-208990 A | 12/2019 |
| JP | 2019-535451 A | 12/2019 |
| JP | 2020-096646 A | 6/2020 |
| JP | 2020-141908 A | 9/2020 |
| TW | 200801571 A | 1/2008 |
| TW | 202018431 A | 5/2020 |
| TW | 202113349 A | 4/2021 |
| WO | 2007/114470 A1 | 10/2007 |
| WO | WO-2011/064683 A2 | 6/2011 |
| WO | WO-2013/005805 A1 | 1/2013 |
| WO | 2014/052267 A1 | 4/2014 |
| WO | WO-2018/098077 A1 | 5/2018 |
| WO | WO-2018/104349 A1 | 6/2018 |
| WO | WO-2019/082276 A1 | 5/2019 |
| WO | WO-2019/097796 A1 | 5/2019 |
| WO | WO-2020/031984 A1 | 2/2020 |

(56)                References Cited

FOREIGN PATENT DOCUMENTS

WO          2021210617 A1    10/2021
WO          2021210618 A1    10/2021

OTHER PUBLICATIONS

Yuewen Sun, "Digital radiography image denoising using a generative adversarial network", Journal of X-Ray Science and Technology, vol. 26, No. 4, Aug. 10, 2018, p. 523-p. 534, XP93154123.
English-language translation of International Preliminary Report on Patentability (IPRP) dated Aug. 24, 2023 that issued in WO Patent Application No. JP2021/037173.
Kenzo Isogawa et al., "Deep Shrinkage Convolutional Neural Network for Adaptive Noise Reduction", IEEE Signal Processing Letters, vol. 25, No. 2, Feb. 1, 2018, p. 224-p. 228, XP055508221.
Xiao-Ping Zhang et al., "Thresholding Neural Network for Adaptive Noise Reduction", IEEE Transactions on Neural Networks, IEEE Service Center, Piscataway, NJ, US, vol. 12, No. 3, May 1, 2001, p. 567-p. 584, XP011039623.
International Preliminary Report on Patentability mailed Oct. 27, 2022 for PCT/JP2021/015464.
International Preliminary Report on Patentability mailed Oct. 27, 2022 for PCT/JP2021/015488.
International Preliminary Report on Patentability mailed Oct. 27, 2022 for PCT/JP2021/015489.
Zhang et al., "FFDNet: Toward a Fast and Flexible Solution for CNN based Image Denoising", arxiv.org, Cornell University Library, 201 Olin Library, Cornell University, Ithaca, NY 14853, Oct. 11, 2017, XP081150272.

Abramova et al, "Analysis of Noise Properties in Dental Images", 2020 IEEE 40th International Conference On Electronics and Nanotechnology (ELNANO), Apr. 22, 2020 May 6, 2020 p. 511-p. 515, XP033769133.
Sungmin Cha et al., "Proceedings of the IEEE/CVF International Conference on Computer Vision (ICCV)", IEEE/CVF, 2019, p. 4160-p. 4169.
Notice of Allowance dated Jan. 6, 2025 that issued in U.S. Appl. No. 17/918,397.
Notice of Allowance dated Jan. 17, 2025 that issued in U.S. Appl. No. 17/918,397.
Hideki Kato et al., "A Presumption Calculating Formula of the X-ray Spectrum Generated from a Molybdenum Target X-ray Tube", The Journal of the Japan Society of Radiological Technology, Mar. 31, 2011, p. 193-p. 201.
Notice of Allowance dated Apr. 18, 2025 in related U.S. Appl. No. 17/918,397.
Lu Qiu_hong et al., "Fault detecting technology based on neurol newtom: algorithm", Optics and Precision Engineering, Feb. 2002, vol. 10, No. 1, p. 25-p. 30 May 29, 2025.
Lu Wei, "High-resolution X-ray digital radiography of electronic industry", School of Information Engineering, Chang'an University, Xi'an 710064, China, Jul. 2012, vol. 33, No. 4, p. 654-p. 659.
Office Action dated Aug. 21, 2025 that issued in U.S. Appl. No. 18/270,897.
Notice of Allowance dated Sep. 23, 2025 for U.S. Appl. No. 17/918,397.
Tabary Joachim et al, "New Functionalities in "SINDBAD" Software for Realistic XRay Simulation Devoted to Complex Parts Inspection", 9TH European Conference on NDT—Sep. 2006, Sep. 25, 2006, XP093363902.
Office Action dated Feb. 16, 2026 in EP Patent Application No. 21789365.0.

* cited by examiner

RADIOGRAPHY METHOD, TRAINED MODEL, RADIOGRAPHY MODULE, RADIOGRAPHY PROGRAM, RADIOGRAPHY SYSTEM, AND MACHINE LEARNING METHOD

TECHNICAL FIELD

An aspect of an embodiment relates to a radiographic image processing method, a trained model, a radiographic image processing module, a radiographic image processing program, a radiographic image processing system, and a machine learning method.

BACKGROUND ART

Since the past, a method of removing noise from image data using a trained model through machine learning such as deep learning has been known (see, for example, the following Patent Literature 1). According to this method, noise from the image data is automatically removed, and thus it is possible to observe a target object with high accuracy.

CITATION LIST

Patent Literature

[Patent Literature 1] Japanese Unexamined Patent Publication No. 2019-91393

SUMMARY OF INVENTION

Technical Problem

In the method of the related art as described above, noise may not be sufficiently removed in a case where a radiographic image generated by transmitting radiation such as X-rays through a target object is used as a target. For example, a relationship between luminance and noise in an image has a tendency to fluctuate depending on the conditions of a radiation source such as an X-ray source, the type of filter being used, and the like, and the noise tends to be difficult to remove effectively.

Consequently, one aspect of an embodiment was contrived in view of such a problem, and an object thereof is to provide a radiographic image processing method, a trained model, a radiographic image processing module, a radiographic image processing program, a radiographic image processing system, and a machine learning method that make it possible to effectively remove noise from a radiographic image.

Solution to Problem

According to one aspect of an embodiment, there is provided a radiographic image processing method including: a step of inputting condition information indicating either conditions of a source of radiation or imaging conditions when the radiation is radiated to capture an image of a target object; a step of calculating average energy related to the radiation passing through the target object on the basis of the condition information; and a step of narrowing down candidates for a trained model from a plurality of trained models constructed through machine learning in advance using image data on the basis of the average energy.

Alternatively, according to another aspect of the embodiment, there is provided a trained model used for the above radiographic image processing method, wherein the trained model is constructed through machine learning using image data and causes a processor to execute image processing for removing noise from a radiographic image of the target object.

Alternatively, according to another aspect of the embodiment, there is provided a radiographic image processing module including: an input unit configured to accept an input of condition information indicating either conditions of a source of radiation or imaging conditions when the radiation is radiated to capture an image of a target object; a calculation unit configured to calculate average energy related to the radiation passing through the target object on the basis of the condition information; and a narrowing unit configured to narrow down candidates for a trained model from a plurality of trained models constructed through machine learning in advance using image data on the basis of the average energy.

Alternatively, according to another aspect of the embodiment, there is provided a radiographic image processing program causing a processor to function as: an input unit configured to accept an input of condition information indicating either conditions of a source of radiation or imaging conditions when the radiation is radiated to capture an image of a target object; a calculation unit configured to calculate average energy related to the radiation passing through the target object on the basis of the condition information; and a narrowing unit configured to narrow down candidates for a trained model from a plurality of trained models constructed through machine learning in advance using image data on the basis of the average energy.

Alternatively, according to another aspect of the embodiment, there is provided a radiographic image processing system including: the above radiographic image processing module; the source configured to radiate radiation to the target object; and an imaging device configured to capture an image of the radiation passing through the target object and acquire the radiographic image.

Alternatively, according to another aspect of the embodiment, there is provided a machine learning method including a construction step of constructing, through machine learning, a trained model for outputting image data from which noise has been removed on the basis of a training image using, as training data, the training image that is a radiographic image of a target object corresponding to average energy related to radiation passing through the target object, the average energy being calculated on the basis of condition information indicating either conditions of a source of the radiation or imaging conditions when the radiation is radiated to capture an image of the target object.

According to the one aspect or the other aspects, the average energy of the radiation passing through the target object is calculated on the basis of the conditions of the source of the radiation or the imaging conditions when a radiographic image of the target object is acquired. Candidates for the trained model used for noise removal are narrowed down from the trained models constructed in advance on the basis of the average energy. Thereby, the trained model corresponding to the average energy of the radiation which is a target for imaging is used for noise removal, and thus it is possible to realize noise removal corresponding to a relationship between luminance and noise in a radiographic image. As a result, it is possible to effectively remove noise from the radiographic image.

Advantageous Effects of Invention

According to the embodiment, it is possible to effectively remove noise from a radiographic image of a target object.

DESCRIPTION OF EMBODIMENTS

Hereinafter, embodiments of the present invention will be described in detail with reference to the accompanying drawings. Meanwhile, in the description, the same elements or elements having the same function are denoted by the same reference signs, and thus duplicate description will be omitted.

Figure 1:
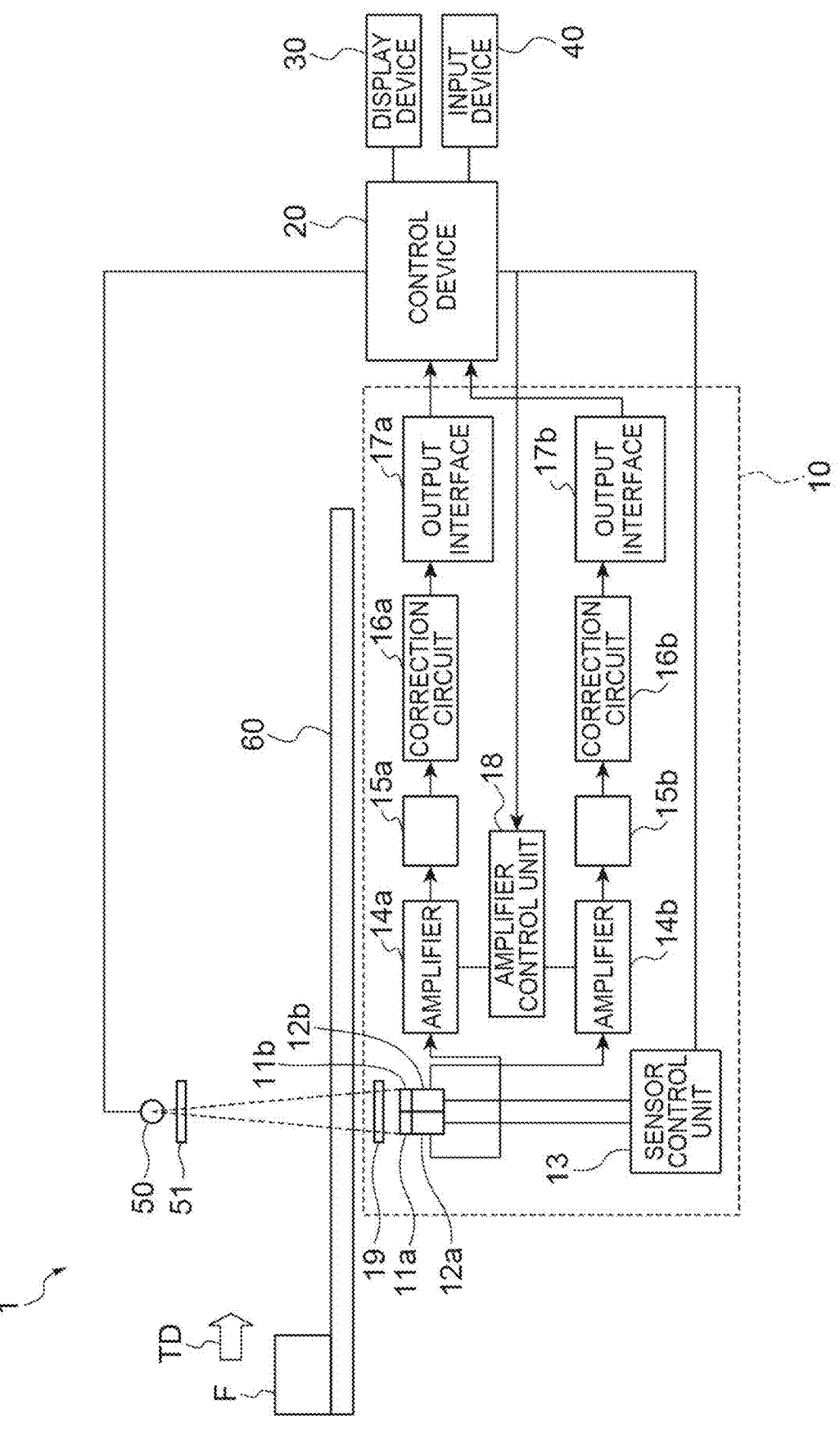
FIG. 1 is a schematic configuration diagram of an image acquisition device 1 according to an embodiment.

FIG. 1 is a configuration diagram of an image acquisition device 1 which is a radiographic image processing system according to the present embodiment. As shown in FIG. 1, the image acquisition device 1 is a device that radiates X-rays (radiation) to a target object F which is transported in a transport direction TD and acquires an X-ray transmission image (radiographic image) obtained by capturing an image of the target object F on the basis of the X-rays passing through the target object F. The image acquisition device 1 performs a foreign substance inspection, a weight inspection, a product inspection, or the like on the target object F using an X-ray transmission image, and examples of the application include food inspection, baggage inspection, substrate inspection, battery inspection, material inspection, and the like. The image acquisition device 1 is configured to include a belt conveyor (transport means) 60, an X-ray irradiator (radiation source) 50, an X-ray detection camera (imaging device) 10, a control device (radiographic image processing module) 20, a display device 30, and an input device 40 for performing various inputs. Meanwhile, the radiographic image in the embodiment of the present invention is not limited to an X-ray image, and may also be an image caused by electromagnetic radiation other than X-rays such as γ-rays.

The belt conveyor 60 has a belt portion on which the target object F is placed, and transports the target object F in the transport direction TD at a predetermined transport speed by moving the belt portion in the transport direction TD. The transport speed of the target object F is, for example, 48 m/min. The belt conveyor 60 can change, as necessary, the transport speed to a transport speed such as, for example, 24 m/min or 96 m/min. In addition, the belt conveyor 60 can appropriately change the height position of the belt portion to change a distance between the X-ray irradiator 50 and the target object F. Meanwhile, examples of the target object F transported by the belt conveyor 60 include foodstuffs such as meat, seafood, agricultural products, or confectionery, rubber products such as tires, resin products, metal products, resource materials such as minerals, waste, and various products such as electronic parts or electronic substrates. The X-ray irradiator 50 is a device that radiates (outputs) X-rays to the target object F as an X-ray source. The X-ray irradiator 50 is a point light source, and diffuses and radiates the X-rays in a predetermined angle range in a fixed irradiation direction. The X-ray irradiator 50 is disposed above the belt conveyor 60 at a predetermined distance from the belt conveyor 60 so that the irradiation direction of the X-rays is directed toward the belt conveyor 60 and the diffused X-rays extend in the entire width direction of the target object F (direction intersecting the transport direction TD). In addition, the X-ray irradiator 50 is configured such that, in the lengthwise direction of the target object F (direction parallel to the transport direction TD), a predetermined division range in the lengthwise direction is set as an irradiation range, and the X-rays are radiated in the entire lengthwise direction of the target object F by the target object F being transported in the transport direction TD by the belt conveyor 60. The X-ray irradiator 50 has a tube voltage and a tube current set by the control device 20, and radiates X-rays having predetermined energy and a radiation dose according to the set tube voltage and tube current toward the belt conveyor 60. In addition, a filter 51 that transmits a predetermined wavelength region of the X-rays is provided in the vicinity of the X-ray irradiator 50 on the belt conveyor 60 side.

The X-ray detection camera 10 detects X-rays passing through the target object F among the X-rays radiated to the target object F by the X-ray irradiator 50, and outputs a signal based on the X-rays. The X-ray detection camera 10 is a dual-line X-ray camera in which two sets of configurations for detecting X-rays are disposed. In the image acquisition device 1 according to the present embodiment, each X-ray transmission image is generated on the basis of the X-rays detected in each line (a first line and a second line) of the dual-line X-ray camera. By performing average processing, addition processing, or the like on the two generated X-ray transmission images, a clear (high-luminance) image can be acquired with a smaller X-ray dose than in a case where an X-ray transmission image is generated on the basis of the X-rays detected in one line.

The X-ray detection camera 10 includes a filter 19, scintillators 11a and 11b, line scan cameras 12a and 12b, a sensor control unit 13, amplifiers 14a and 14b, AD converters 15a and 15b, correction circuits 16a and 16b, output interfaces 17a and 17b, and an amplifier control unit 18. The scintillator 11a, the line scan camera 12a, the amplifier 14a, the AD converter 15a, the correction circuit 16a, and the output interface 17a are electrically connected to each other, and have components related to the first line. In addition, the scintillator 11b, the line scan camera 12b, the amplifier 14b, the AD converter 15b, the correction circuit 16b, and the output interface 17b are electrically connected to each other, and have components related to the second line. The line scan camera 12a of the first line and the line scan camera 12b of the second line are disposed side by side along the transport direction TD. Meanwhile, hereinafter, the components of the first line will be described to represent components common to the first line and the second line.

The scintillator 11a is fixed on the line scan camera 12a by adhesion or the like, and converts the X-rays passing through the target object F into scintillation light. The scintillator 11a outputs the scintillation light to the line scan camera 12a. The filter 19 transmits a predetermined wavelength region of the X-rays toward the scintillator 11a.

The line scan camera 12a detects the scintillation light from the scintillator 11a, converts the detected light into electric charge, and outputs it as a detection signal (electrical signal) to the amplifier 14a. The line scan camera 12a has a plurality of line sensors arranged in parallel in a direction intersecting the transport direction TD. The line sensor is, for example, a charge coupled device (CCD) image sensor, a complementary metal-oxide semiconductor (CMOS) image sensor, or the like, and includes a plurality of photodiodes.

The sensor control unit 13 controls the line scan cameras 12a and 12b to repeatedly capture images at a predetermined detection period so that the line scan cameras 12a and 12b can capture an image of X-rays passing through the same region of the target object F. As the predetermined detection period, for example, a period common to the line scan cameras 12a and 12b may be set on the basis of the distance between the line scan cameras 12a and 12b, the speed of the belt conveyor 60, the distance between the X-ray irradiator 50 and the target object F on the belt conveyor 60 (focus object distance (FOD)), and the distance between the X-ray irradiator 50 and the line scan cameras 12a and 12b (focus detector distance (FDD)). In addition, the predetermined period may be individually set on the basis of the pixel width of a photodiode in a direction perpendicular to the arrangement direction of pixels of the line sensors of the line scan cameras 12a and 12b. In this case, the deviation (delay time) of the detection period between the line scan cameras 12a and 12b may be specified in accordance with the distance between the line scan cameras 12a and 12b, the speed of the belt conveyor 60, the distance between the X-ray irradiator 50 and the target object F on the belt conveyor 60 (FOD), and the distance between the X-ray irradiator 50 and the line scan cameras 12a and 12b (FDD), and individual periods may be set for each. The amplifier 14a amplifies the detection signal at a predetermined set amplification factor to generate an amplified signal, and outputs the amplified signal to the AD converter 15a. The set amplification factor is an amplification factor which is set by the amplifier control unit 18. The amplifier control unit 18 sets the set amplification factor of the amplifiers 14a and 14b on the basis of predetermined imaging conditions.

The AD converter 15a converts the amplified signal (voltage signal) output by the amplifier 14a into a digital signal, and outputs the converted signal to the correction circuit 16a. The correction circuit 16a performs a predetermined correction such as signal amplification on the digital signal, and outputs the corrected digital signal to the output interface 17a. The output interface 17a outputs the digital signal to the outside of the X-ray detection camera 10. In FIG. 1, the AD converter, the correction circuit, and the output interface exist individually, but they may be integrated into one.

The control device 20 is a computer such as, for example, a personal computer (PC). The control device 20 generates an X-ray transmission image on the basis of the digital signal (amplified signal) output from the X-ray detection camera 10 (more specifically, the output interfaces 17a and 17b). The control device 20 generates one X-ray transmission image by performing average processing or addition processing on two digital signals output from the output interfaces 17a and 17b. The generated X-ray transmission image is output to the display device 30 after a noise removal process to be described later is performed, and is displayed by the display device 30. In addition, the control device 20 controls the X-ray irradiator 50, the amplifier control unit 18, and the sensor control unit 13. Meanwhile, the control device 20 of the present embodiment is a device which is independently provided outside the X-ray detection camera 10, but it may be integrated inside the X-ray detection camera 10.

Figure 2:
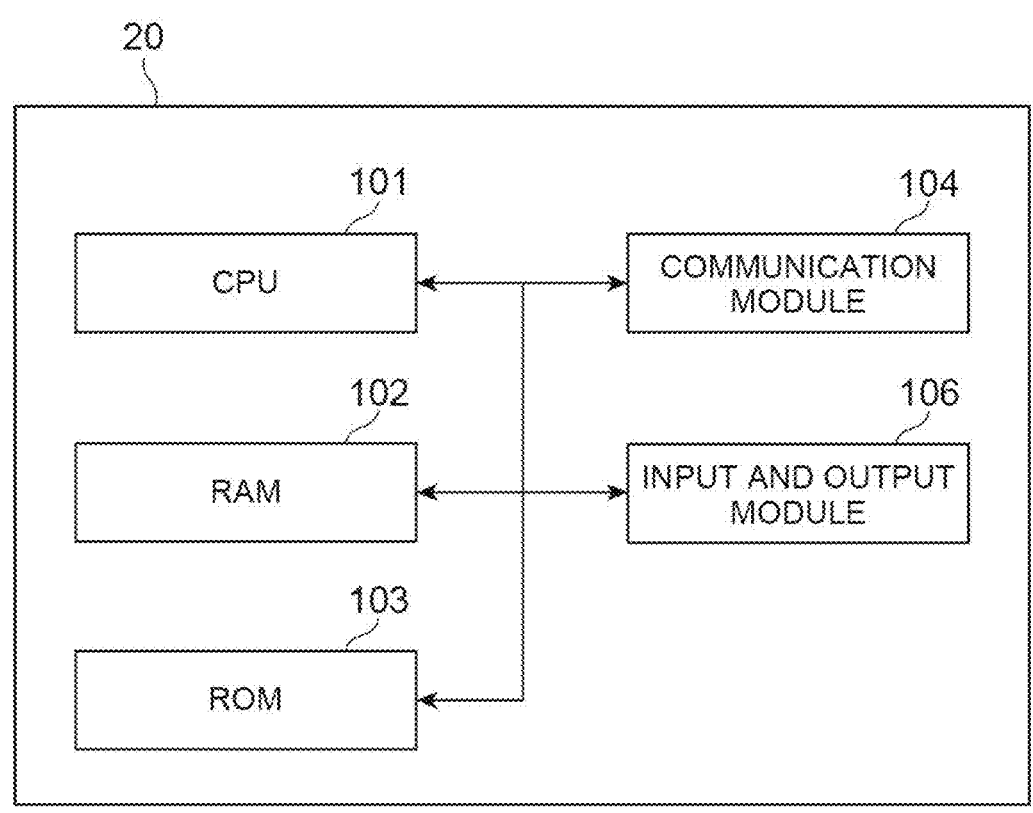
FIG. 2 is a block diagram illustrating an example of a hardware configuration of a control device 20 of FIG. 1.

FIG. 2 shows a hardware configuration of the control device 20. As shown in FIG. 2, the control device 20 is a computer or the like physically including a central processing unit (CPU) 101 which is a processor, a random access memory (RAM) 102 or a read only memory (ROM) 103 which is a recording medium, a communication module 104, an input and output module 106, and the like, which are electrically connected to each other. Meanwhile, the control device 20 may include a display, a keyboard, a mouse, a touch panel display, and the like as the input device 40 and the display device 30, or may include a data recording device such as a hard disk drive or a semiconductor memory. In addition, the control device 20 may be constituted by a plurality of computers.

Figure 3:
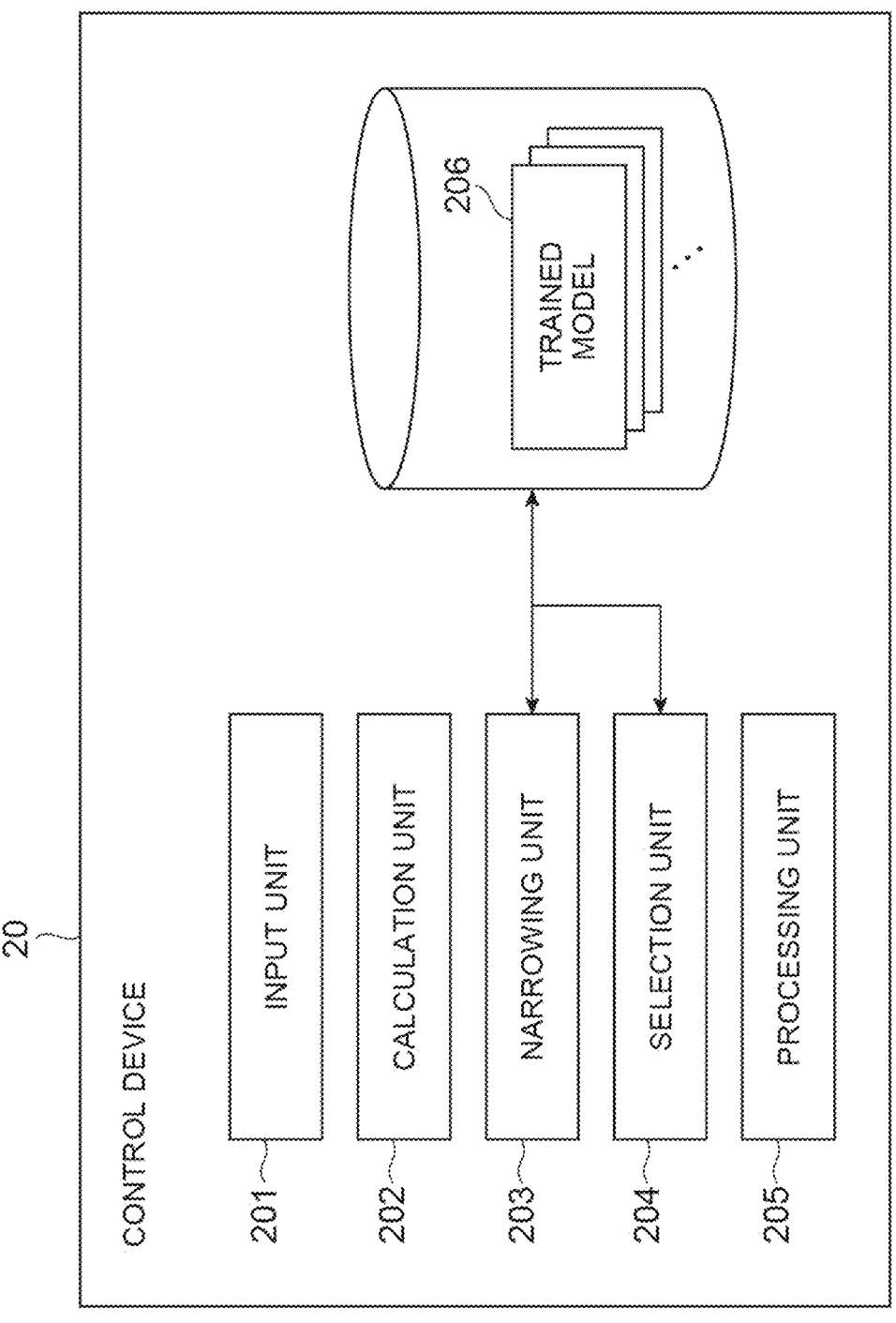
FIG. 3 is a block diagram illustrating a functional configuration of the control device 20 of FIG. 1.

FIG. 3 is a block diagram illustrating a functional configuration of the control device 20. The control device 20 includes an input unit 201, a calculation unit 202, a narrowing unit 203, a selection unit 204, and a processing unit 205. Each functional unit of the control device 20 shown in FIG. 3 is realized by loading a program (a radiographic image processing program of the present embodiment) on the hardware such as the CPU 101 and the RAM 102 to thereby bring the communication module 104, the input and output module 106, and the like into operation under the control of the CPU 101 and read out and write data in the RAM 102. The CPU 101 of the control device 20 causes the control device 20 to function as each functional unit in FIG. 3 by executing this computer program, and sequentially executes processing corresponding to a radiographic image processing method to be described later. Meanwhile, the CPU may be a single piece of hardware, or may be implemented in a programmable logic such as an FPGA like a soft processor. The RAM or the ROM may also be a single piece of hardware, or may be built into a programmable logic such as an FPGA. Various types of data required for executing this computer program and various types of data generated by executing this computer program are all stored in a built-in memory such as the ROM 103 or the RAM 102, or a storage medium such as a hard disk drive.

In addition, a plurality of trained models 206 which are loaded by the CPU 101 to cause the CPU 101 to execute a noise removal process for an X-ray transmission image are stored in advance in the control device 20. Each of the plurality of trained models 206 is a learning model based on machine learning constructed in advance using image data as training data. Examples of machine learning include supervised learning, deep learning, reinforcement learning, neural network learning, and the like. In the present embodiment, the two-dimensional convolutional neural network described in the paper "Beyonda Gaussian Denoiser: Residual Learning of Deep CNN for Image Denoising" authored by Kai Zhang et al. is adopted as an example of a deep learning algorithm. The plurality of trained models 206 may be generated by an external computer or the like and downloaded to the control device 20, or may be generated in the control device 20.

Figure 4:
FIG. 4 is a diagram illustrating an example of image data which is training data used to construct trained models 206 of FIG. 3.

FIG. 4 shows an example of image data which is training data used to construct trained models 206. As the training data, an X-ray transmission image having a pattern of various thicknesses, various materials, and various resolutions as an imaging target can be used. The example shown in FIG. 4 is an example of an X-ray transmission image generated for chicken. As the image data, an X-ray transmission image actually generated for a plurality of types of target objects using the image acquisition device 1 may be used, or image data generated by simulation calculation may be used. The X-ray transmission image may be acquired using a device different from the image acquisition device 1. In addition, the X-ray transmission image and the image data generated by simulation calculation may be used in combination. Each of the plurality of trained models 206 is constructed in advance using image data obtained for transmitted X-rays having different average energy and having a known noise distribution. The average energy of X-rays in the image data is set to a different value in advance by setting the operating conditions of the X-ray irradiator (radiation source) 50 of the image acquisition device 1, the imaging conditions of the image acquisition device 1, or the like, or setting the operating conditions or imaging conditions of the X-ray irradiator 50 during simulation calculation (a method of setting average energy according to the operating conditions or imaging conditions will be described later). That is, the plurality of trained models 206 are constructed through machine learning using, as training data, a training image which is an X-ray image corresponding to average energy related to X-rays passing through the target object F calculated on the basis of condition information indicating the operating conditions of the X-ray irradiator (radiation source) 50 when the X-ray transmission image of the target object F is captured, the imaging conditions of the X-ray detection camera 10, or the like (construction step). For example, in the present embodiment, each of the plurality of trained models 206 is constructed using multiple frames (for example, 20,000 frames) of a plurality of types of image data in which the average energy is 10 keV, 20 keV, 30 keV, . . . and values in increments of 10 keV are set.

Figure 5:
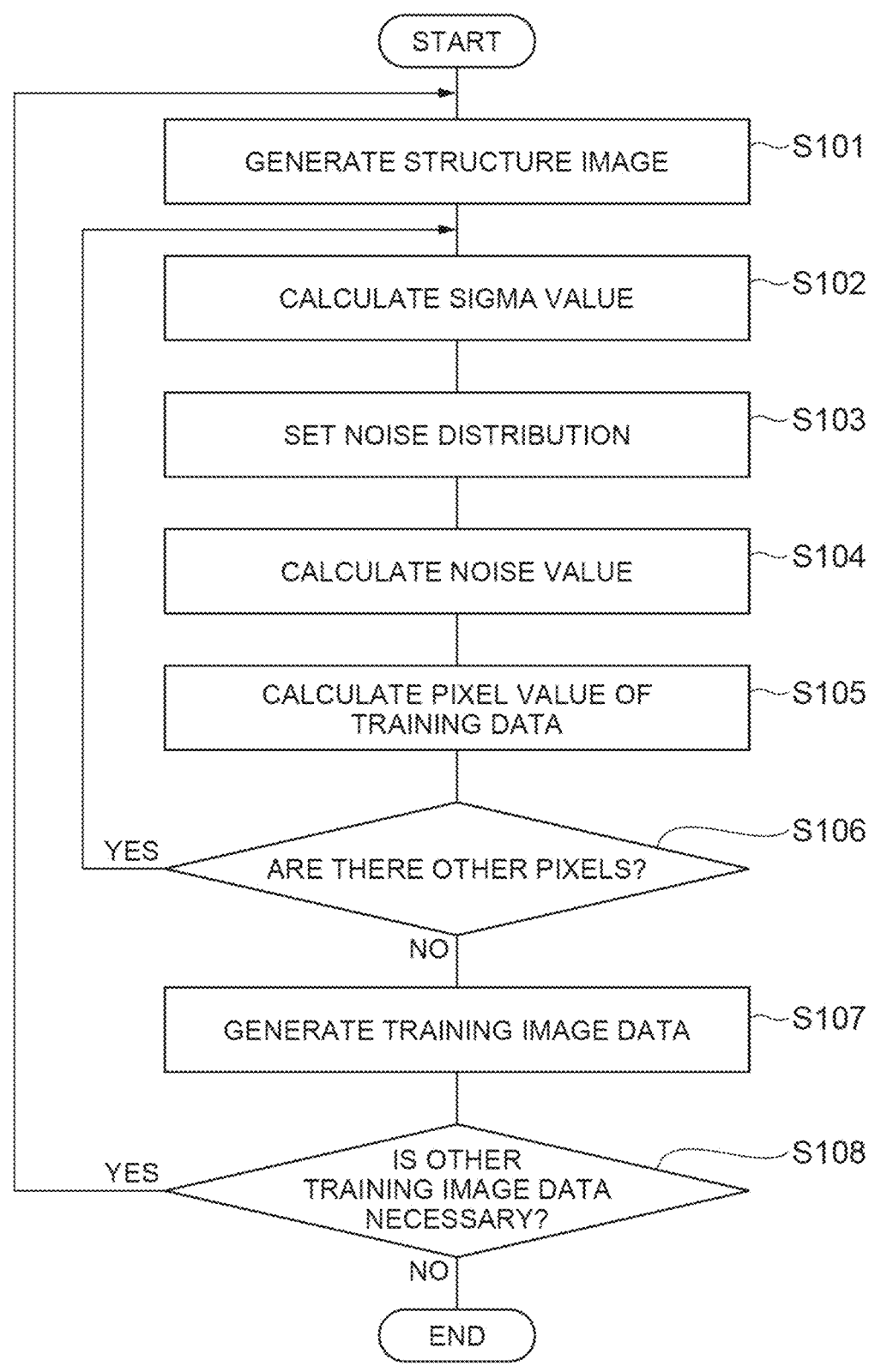
FIG. 5 is a flowchart illustrating a procedure of creating image data which is training data used to construct the trained models 206 of FIG. 3.

FIG. 5 is a flowchart illustrating a procedure of creating image data which is training data used to construct the trained models 206.

The image data (also referred to as training image data) which is training data is created by a computer in the following procedure. First, an image of a structural body having a predetermined structure (structure image) is created (step S101). For example, an image of a structural body having a predetermined structure may be created by simulation calculation. In addition, an X-ray image of a structure such as a chart having a predetermined structure may be acquired to create a structure image. Next, a sigma value which is a standard deviation of pixel values is calculated for one pixel selected from a plurality of pixels constituting such a structure image (step S102). A normal distribution (Poisson distribution) indicating a noise distribution is then set on the basis of the sigma value obtained in step S102 (step S103). In this manner, training data for various noise conditions can be generated by setting the normal distribution on the basis of the sigma value. Subsequently, a noise value which is set at random is calculated along the normal distribution which is set on the basis of the sigma value in step S103 (step S104). Further, the noise value obtained in step S104 is added to the pixel value of one pixel to generate pixel values constituting the image data which is training data (step S105). The processes of steps S102 to S105 are performed for each of a plurality of pixels constituting the structure image (step S106), and training image data serving as training data is generated (step S107). In addition, in a case where the training image data is further required, it is determined that the processes of steps S101 to S107 are performed on another structure image (step S108), and another training image data serving as training data is generated. Meanwhile, the other structure image may be an image of a structural body having the same structure, or may be an image of a structural body having another structure.

Meanwhile, it is necessary to prepare a large number of pieces of image data which is training data used to construct the trained model 206. In addition, the structure image is preferably an image with less noise, ideally an image without noise. Therefore, when a structure image is generated through simulation calculation, many images without noise can be generated, and thus it is effective to generate a structure image through simulation calculation.

Hereinafter, referring back to FIG. 3, the details of the function of each functional unit of the control device 20 will be described.

The input unit 201 accepts an input of condition information indicating the operating conditions of the X-ray irradiator (radiation source) 50 when the X-ray transmission image of the target object F is captured, the imaging conditions of the X-ray detection camera 10, or the like from a user of the image acquisition device 1. Examples of the operating conditions include all or some of a tube voltage, a target angle, a target material, and the like. Examples of the condition information indicating the imaging conditions include all or some of information relating to the material and thickness of the filters 51 and 19 (a filter included in a camera used to capture an image of a target object or a filter included in a source) disposed between the X-ray irradiator 50 and the X-ray detection camera 10, the distance (FDD) between the X-ray irradiator 50 and the X-ray detection camera 10, and the type of window material of the X-ray detection camera 10, and the material and thickness of the scintillators 11*a* and 11*b* of the X-ray detection camera 10, X-ray detection camera information (for example, a gain setting value, a circuit noise value, an amount of saturated charge, a conversion coefficient value (number of electrons/ count), and the line rate (Hz) or line speed (m/min) of the camera), and information on the target object, and the like. The input unit 201 may accept an input of the condition information as a direct input of information such as numerical values, or may accept the input as a selective input for information such as numerical values which are set in an internal memory in advance. The input unit 201 acquires the input of the above condition information from a user, but it may accept some condition information (such as a tube voltage) in accordance with the detection result of the state of control performed by the control device 20.

The calculation unit 202 calculates the value of the average energy of X-rays (radiation) that pass through the target object F using the image acquisition device 1 and are detected by the X-ray detection camera 10 on the basis of the condition information accepted by the input unit 201. For example, the calculation unit 202 calculates an X-ray spectrum of the X-ray detected by the X-ray detection camera 10 using, for example, a known approximate expression of Tucker and others on the basis of information such as a tube voltage, a target angle, a target material, the material and thickness of a filter and its presence or absence, the type of a window material and its presence or absence, and the material and thickness of the scintillators 11*a* and 11*b* of the X-ray detection camera 10 which are included in the condition information. The calculation unit 202 further calculates a spectral intensity integration value and a photon number integration value from the spectrum of the X-rays, and calculates the value of the average energy of the X-rays by dividing the spectral intensity integration value by the photon number integration value.

A calculation method using a known approximate expression of Tucker will be described. For example, in a case where the target is specified as tungsten and the target angle is specified as 25°, the calculation unit 202 can determine Em: kinetic energy during electron target collision, T: electron kinetic energy in the target, A: proportionality constant determined by the atomic number of the target substance, $\rho$: the density of the target, $\mu(E)$: the linear attenuation coefficient of the target substance, B: the function of Z and T that changes gently, C: Thomson-Whiddington constant, $\theta$: target angle, and c: the speed of light in vacuum. Further, the calculation unit 202 can calculate an irradiation X-ray spectrum by calculating the following Expression (1) on the basis of these values.

[Expression 1]

$$\varphi(E) = A \cdot \int_{fi}^{Em} \left( \frac{T + m_0 c^2}{T} \right) \cdot B \cdot \left( \frac{1}{\rho} \frac{dT}{dx} \right)^{-1} \exp\left\{ -\mu(E) \frac{\left(E_m^2 - T^2\right)}{\rho C \sin(\theta + \varphi)} \right\} dT \quad (1)$$

Meanwhile, Em can be determined from information on the tube voltage, A, $\rho$, and $\mu(E)$ can be determined from information on the target material, and $\theta$ can be determined from information on the target angle.

Next, the calculation unit 202 can calculate the X-ray energy spectrum that passes through the filter and the target object F and is absorbed by the scintillator by using the X-ray attenuation expression of the following Expression (2).

[Expression 2]

$$I = I_0 e^{-\mu x} \quad (2)$$

Here, $\mu$ is the attenuation coefficient of the subject substance, the filter, the scintillator, or the like, and x is the thickness of the subject substance, the filter, the scintillator, or the like. In addition, $\mu$ can be determined from information on the materials of the target object, the filter, and the scintillator, and x can be determined from information on the thicknesses of the target object, the filter, and the scintillator. The X-rays photon number spectrum can be obtained by dividing this X-ray energy spectrum by energy of each X-ray. The calculation unit 202 calculates the average energy of X-rays using the following Expression (3) by dividing the integration value of energy intensity by the integration value of the number of photons.

Average energy $E$=spectral intensity integration value/photon number integration value    (3)

The calculation unit 202 calculates the average energy of X-rays through the above calculation process. Meanwhile, for the calculation of the X-ray spectrum, a known approximate expression of Kramers or Birch et al. may be used.

The narrowing unit 203 narrows down candidates for the trained model from the plurality of trained models 206 constructed in advance on the basis of the value of the average energy calculated by the calculation unit 202. That is, the narrowing unit 203 compares the calculated average energy value with the value of the X-ray average energy in the image data used to construct the plurality of trained models 206, and narrows down a plurality of trained models 206 constructed by image data having similar average energy values as candidates. More specifically, in a case where the average energy value calculated by the calculation unit 202 is 53 keV, the narrowing unit 203 uses trained models 206 constructed by image data having average energy values of 40 keV, 50 keV, and 60 keV whose difference from the value is less than a predetermined threshold (for example, 15 keV) as candidates for the trained model.

The selection unit 204 selects trained models 206 to be finally used for a noise removal process of the X-ray transmission image of the target object F from the candidates narrowed down by the narrowing unit 203. Specifically, the selection unit 204 acquires an X-ray transmission image captured by radiating X-rays to a jig in the image acquisition device 1, and selects trained models 206 to be finally used on the basis of the image characteristics of the X-ray transmission image. In this case, the selection unit 204 analyzes energy characteristics, noise characteristics, resolution characteristics, or the like as the image characteristics of the X-ray transmission image, and selects trained models 206 on the basis of the analysis result.

More specifically, the selection unit 204 acquires an X-ray transmission image for a flat plate-like member as a jig whose thickness and material is known and whose relationship between the average energy of X-rays and the transmittance of X-rays is known, compares the luminance of the X-ray image passing through the jig with the luminance of the X-ray image passing through the air, and calculates the transmittance of X-rays at one point (or the average of a plurality of points) in the jig. For example, in a case where the luminance of the X-ray image passing through the jig is 5,550 and the luminance of the X-ray image passing through the air is 15,000, the transmittance is calculated to be 37%. The selection unit 204 then specifies the average energy (for example, 50 keV) of transmitted X-rays estimated from the transmittance of 37% as the energy characteristics of the X-ray transmission image of the jig. The selection unit 204 selects one trained model 206 constructed by image data of average energy closest to the specified average energy value.

Figure 6:
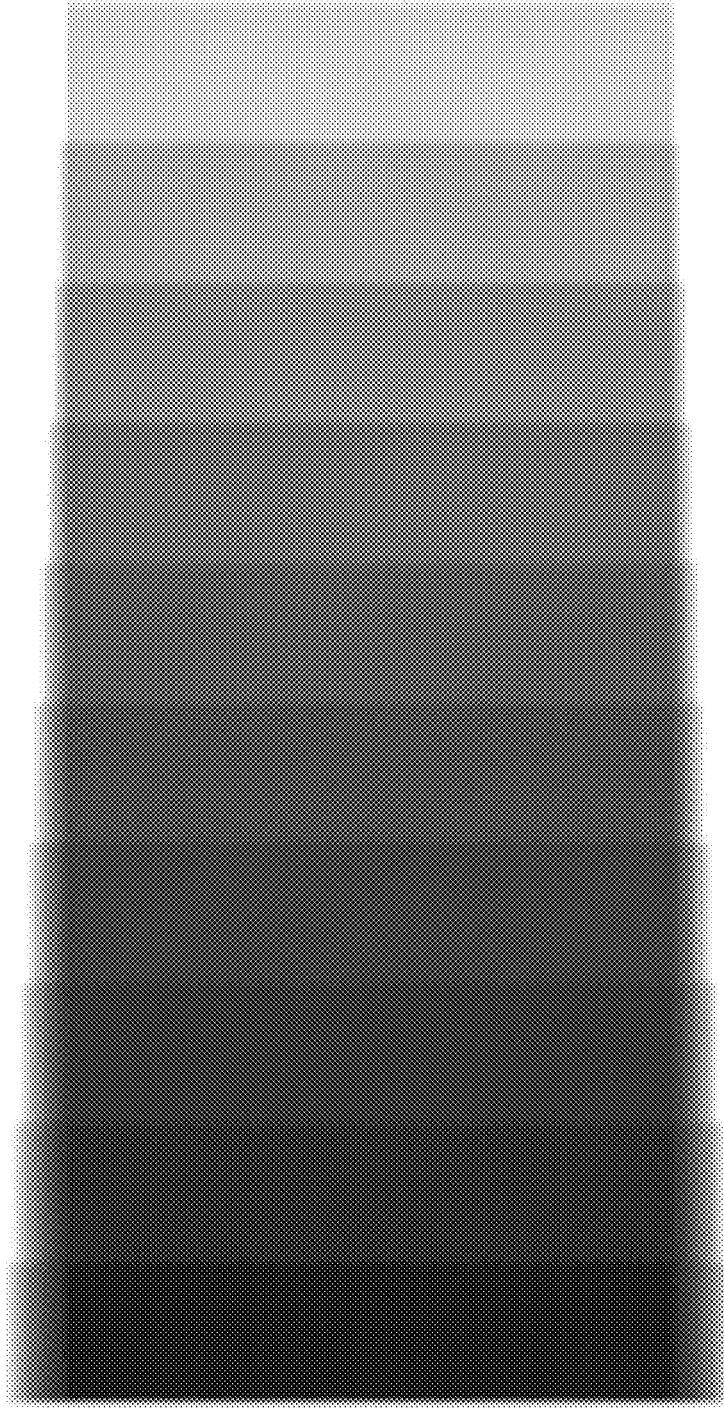
FIG. 6 is a diagram illustrating an example of an X-ray transmission image to be analyzed by a selection unit 204 of FIG. 3.
Figure 7:
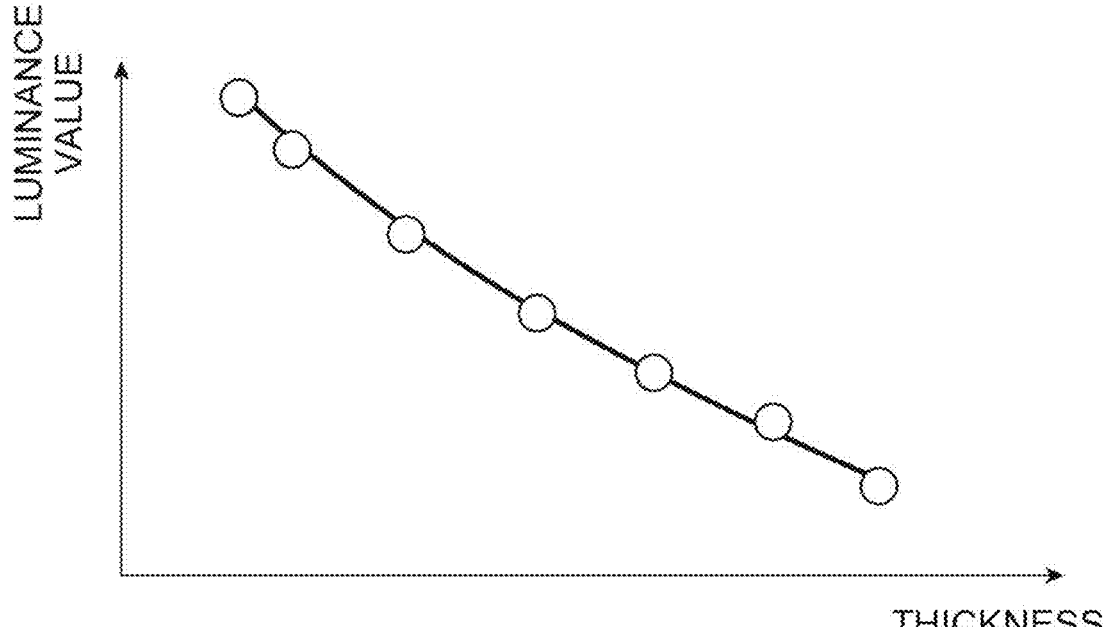
FIG. 7 is a diagram illustrating an example of a characteristic graph of thickness and luminance acquired by the selection unit 204 of FIG. 3.

In addition, the selection unit 204 may analyze the characteristics at a plurality of points of the jig whose thickness or material changes as the energy characteristics of the X-ray transmission image of the jig. FIG. 6 is a diagram illustrating an example of an X-ray transmission image to be analyzed by the selection unit 204. FIG. 6 is an X-ray transmission image for a jig having a shape in which the thickness changes stepwise. The selection unit 204 selects a plurality of measurement regions (regions of interest (ROI)) having different thicknesses from such an X-ray transmission image, analyzes the luminance average value for each of the plurality of measurement regions, and acquires a characteristic graph of thickness-luminance as energy characteristics. FIG. 7 shows an example of a characteristic graph of thickness and luminance acquired by the selection unit 204.

Further, the selection unit 204 similarly acquires a characteristic graph of thickness and luminance for the image data used to construct the trained model 206 narrowed down by the narrowing unit 203, and selects trained models 206 constructed by image data having characteristics closest to the characteristic graph acquired for the jig as final trained models 206. However, the image characteristics of the image data used to construct the trained models 206 may refer to those calculated in advance outside the control device 20. By setting a plurality of measurement regions in this way, it is possible to select the best trained model for noise removal of the X-ray transmission image of the target object F. Particularly, it is possible to accurately estimate a difference in the X-ray spectrum or a difference in the effect of the filter during measurement of the X-ray transmission image.

Figure 8:
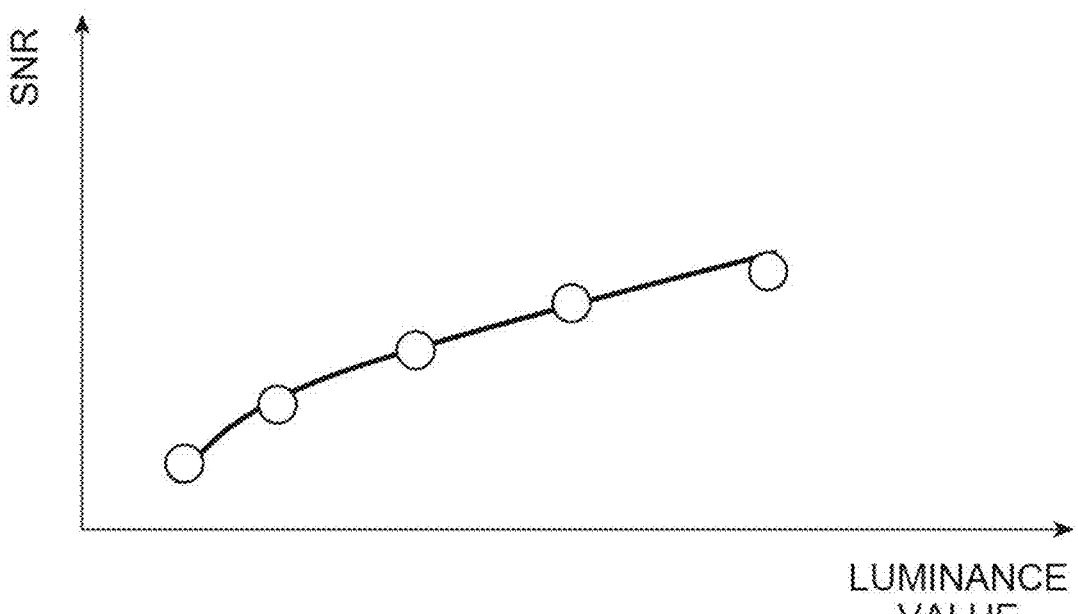
FIG. 8 is a diagram illustrating an example of a characteristic graph of luminance and SNR acquired by the selection unit 204 of FIG. 3.

In addition, the selection unit 204 can also analyze the luminance value and noise for each of the plurality of measurement regions as the noise characteristics of the X-ray transmission image of the jig, and acquire a characteristic graph of luminance and a noise ratio as the noise characteristics. That is, the selection unit 204 selects a plurality of measurement regions ROI having different thicknesses or materials from the X-ray transmission image, analyzes the standard deviation of the luminance values of the plurality of measurement regions ROI and the average value of the luminance values thereof, and acquires a characteristic graph of luminance–SN ratio (SNR) as the noise characteristics. In this case, the selection unit 204 calculates the SNR for each measurement region ROI using SNR=(average value of luminance values)÷(standard deviation of luminance values). FIG. 8 shows an example of a characteristic graph of luminance and SNR acquired by the selection unit 204. The selection unit 204 then selects trained model 206 constructed by image data having the noise characteristics closest to the acquired characteristic graph as final trained model 206.

Here, the selection unit 204 may acquire a characteristic graph in which the vertical axis is noise calculated from the standard deviation of the luminance values, as the noise characteristics, instead of the above characteristic graph of luminance and SNR. By using such a characteristic graph of luminance-noise, it is possible to specify a dominant noise factor (such as shot noise or readout noise) from the slope of the graph in the region of each signal amount with respect to each signal amount detected by the X-ray detection camera 10, and to select trained models 206 on the basis of the specified result.

Figure 9:
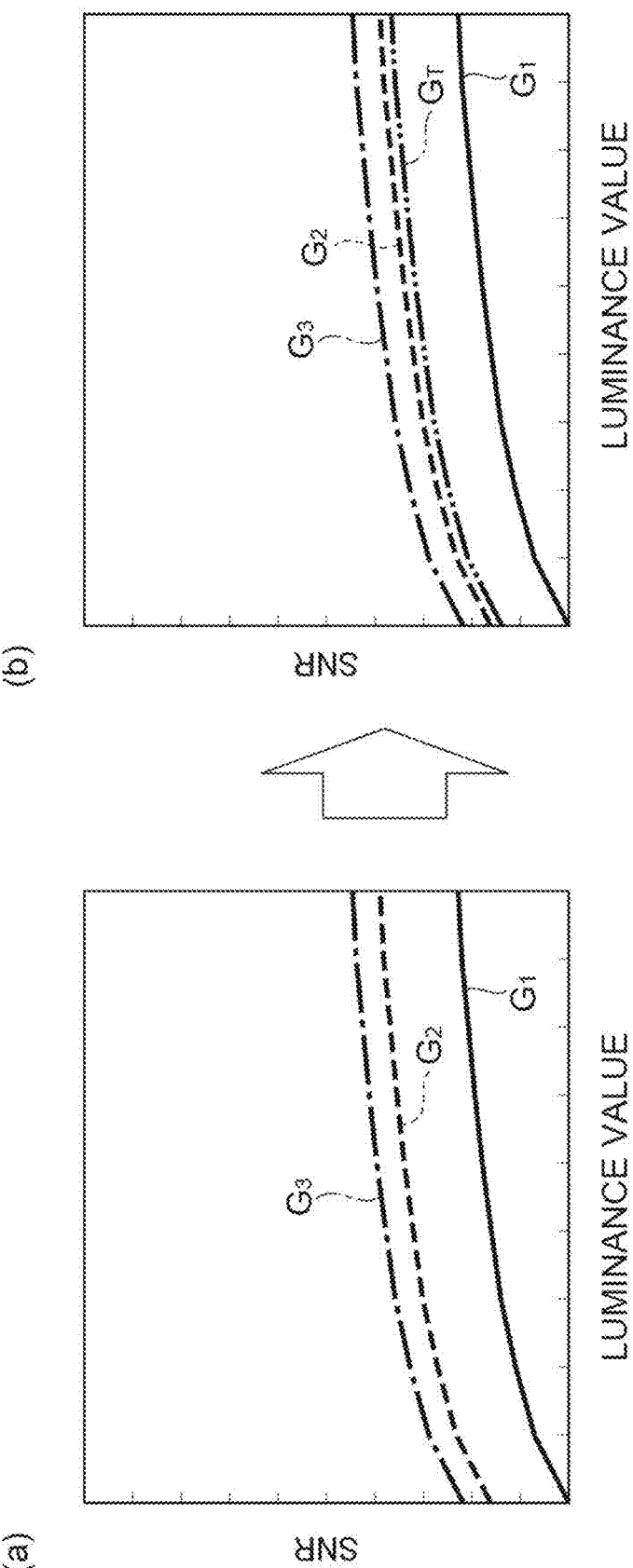
FIG. 9 is a diagram illustrating a function of selection of a trained model based on image characteristics which is performed by the selection unit 204 of FIG. 3.

FIG. 9 is a diagram illustrating a function of selection of a trained model based on image characteristics which is performed by the selection unit 204. In FIG. 9, the part (a)

shows characteristic graphs $G_1$, $G_2$, and $G_3$ of luminance and SNR of image data used to construct the plurality of trained models 206, and the part (b) shows a characteristic graph $G_T$ of luminance and SNR of the X-ray transmission image obtained by capturing an image of the jig in addition to these characteristic graphs $G_1$, $G_2$, and $G_3$. In a case where such characteristic graphs $G_1$, $G_2$, $G_3$, and $G_T$ are targeted, the selection unit 204 functions so as to select trained models 206 constructed by image data of the characteristic graph $G_2$ closest to the characteristics of the characteristic graph $G_T$. At the time of selection, the selection unit 204 calculates an SNR error for each luminance value at regular intervals between each of the characteristic graphs $G_1$, $G_2$, and $G_3$ and the characteristic graph $G_T$, calculates the root mean squared error (RMSE) of these errors, and selects trained models 206 corresponding to the characteristic graphs $G_1$, $G_2$, and $G_3$ having the smallest root mean squared error. In addition, even in a case where the selection is performed using the energy characteristics, the selection unit 204 can select trained models 206 in the same way.

The selection unit 204 can also select trained model 206 on the basis of the characteristics of an image after a plurality of trained models are applied to the X-ray transmission image of the jig and the noise removal process is executed.

Figure 10:
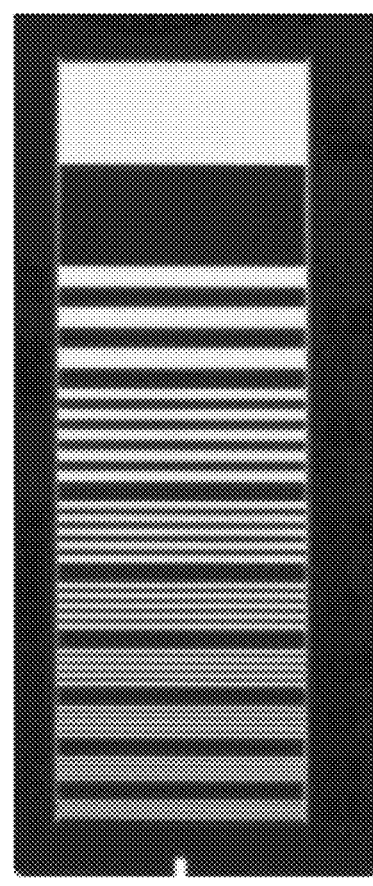
FIG. 10 is a diagram illustrating an example of an X-ray transmission image used for the evaluation of resolution which is performed by the selection unit 204 of FIG. 3.

For example, the selection unit 204 uses the X-ray transmission image obtained by capturing an image of the jig having charts of various resolutions to apply a plurality of trained models 206 to the image and evaluate the resulting image after noise removal. The selection unit 204 then selects trained model 206 used for an image having the smallest change in resolution before and after the noise removal process. FIG. 10 shows an example of an X-ray transmission image used for the evaluation of resolution. In this X-ray transmission image, a chart whose resolution changes stepwise in one direction is used as an imaging target. The resolution of the X-ray transmission image can be measured using a modulation transfer function (MTF) or a contrast transfer function (CTF).

Figure 11:
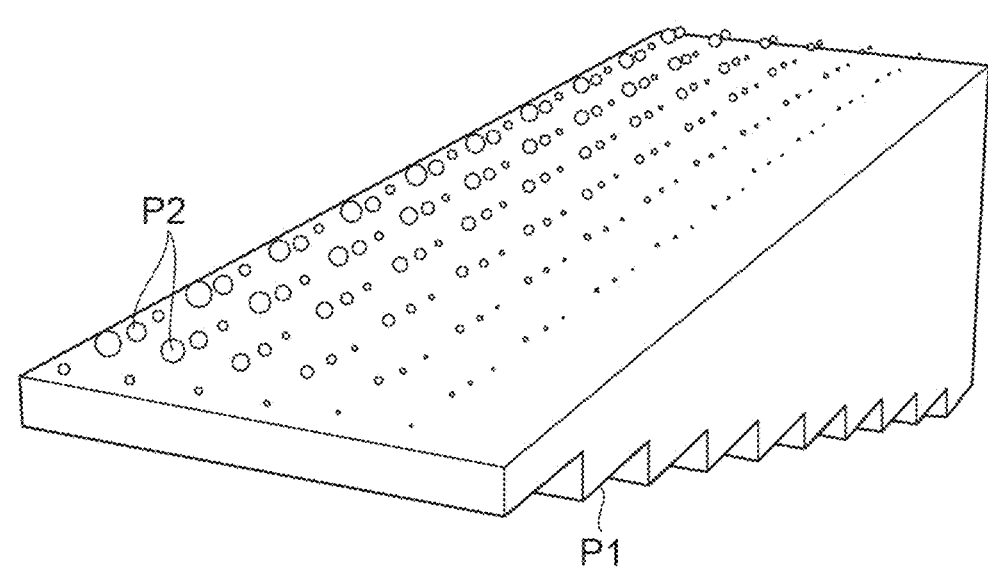
FIG. 11 is a perspective view illustrating an example of a structure of a jig used for the evaluation of luminance and a noise ratio which is performed by the selection unit 204 of FIG. 3.
Figure 12:
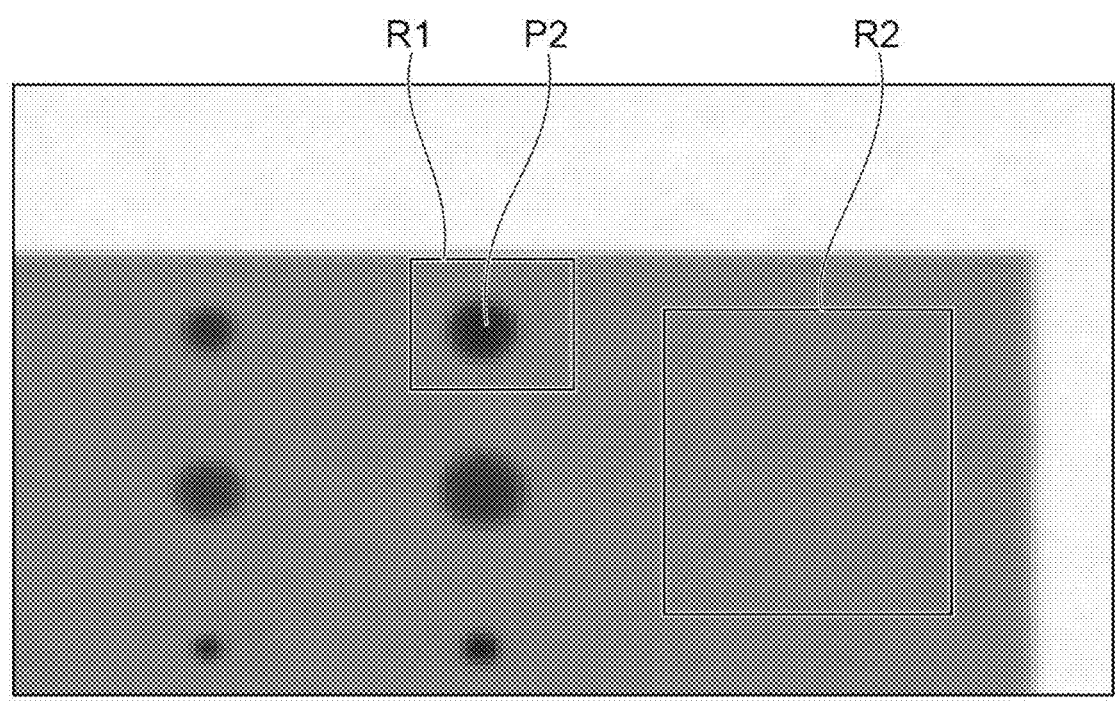
FIG. 12 is a diagram illustrating an X-ray transmission image after a noise removal process obtained for the jig of FIG. 11.

In addition to the evaluation of the above change in resolution, the selection unit 204 may evaluate the characteristics of the luminance and a noise ratio of the image after noise removal and select trained model 206 used to generate an image having the highest characteristics. FIG. 11 shows an example of the structure of the jig used for the evaluation of the luminance and a noise ratio. For example, as the jig, a jig in which foreign substances P2 having various materials and various sizes are scattered in a member P1 whose thickness changes stepwise in one direction can be used. FIG. 12 shows an X-ray transmission image obtained for the jig of FIG. 11 after the noise removal process. The selection unit 204 selects an image region R1 containing an image of the foreign substance P2 in the X-ray transmission image and an image region R2 not containing an image of the foreign substance P2 in the vicinity of the region R1, and calculates the minimum value $L_{MIN}$ of luminance in the image region R1, the average value $L_{AVE}$ of luminance in the image region R2, and the standard deviation $L_{SD}$ of luminance in the image region R2. The selection unit 204 calculates the luminance and a noise ratio CNR using the following expression.

$$CNR = (L_{AVE} - L_{MIN})/L_{SD}$$

Further, the selection unit 204 calculates the luminance and a noise ratio CNR for each of the X-ray transmission images after the application of the plurality of trained models 206, and selects trained models 206 used to generate an X-ray transmission image having the highest luminance and a noise ratio CNR.

Alternatively, the selection unit 204 may perform the calculation using the following expression on the basis of the average value $L_{AVE\_R1}$ of luminance in the image region R1, the average value $L_{AVE\_R2}$ of luminance in the image region R2, and the standard deviation $L_{SD}$ of luminance in the image region R2.

$$\text{CNR}=(L_{AVE\_R1}-L_{MIN\_R2})/L_{SD}$$

The processing unit 205 applies the trained models 206 selected by the selection unit 204 to the X-ray transmission image acquired for the target object F, and generates an output image by executing image processing for removing noise. The processing unit 205 then outputs the generated output image to the display device 30 or the like.

Figure 13:
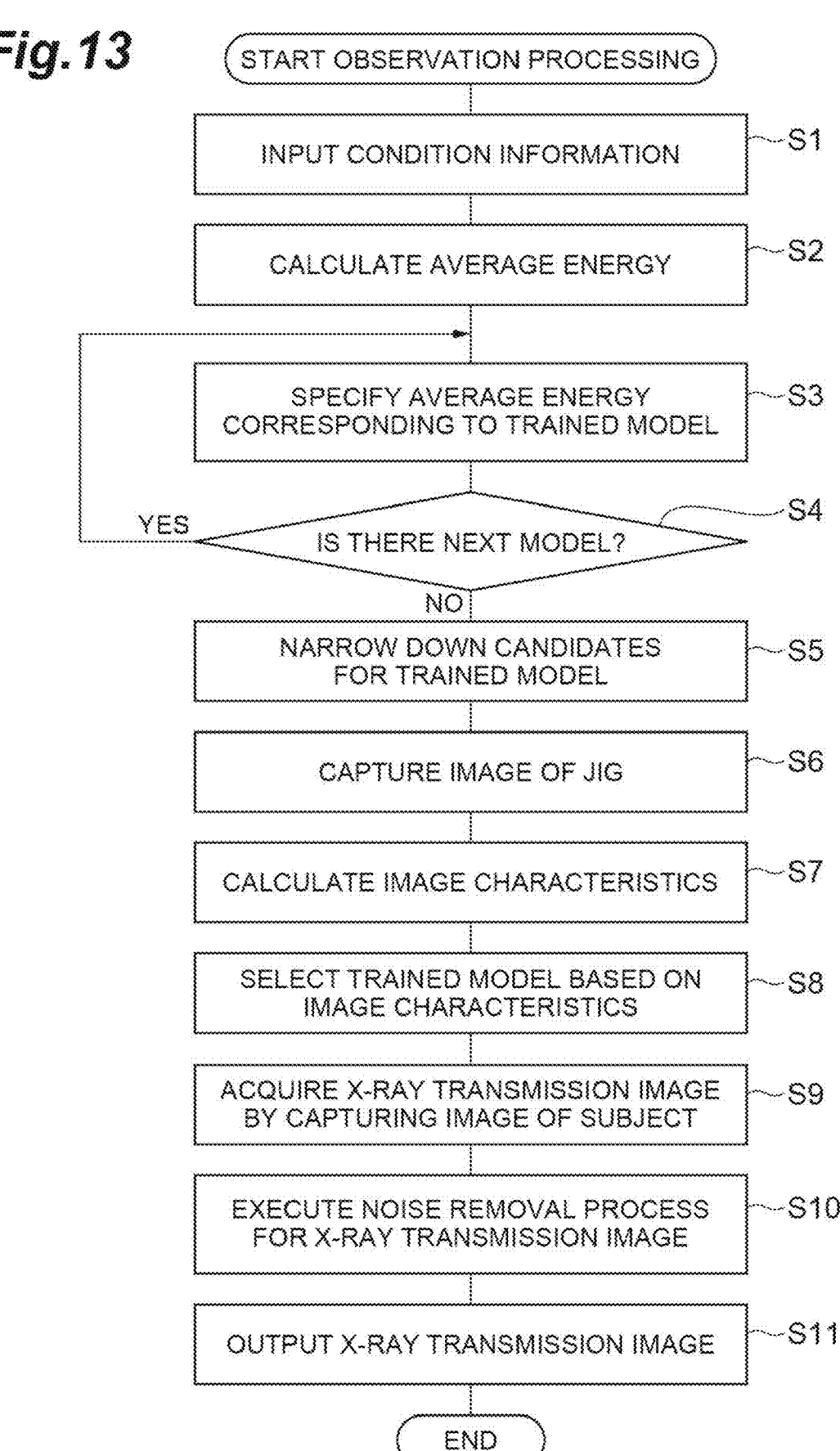
FIG. 13 is a flowchart illustrating a procedure of observation processing using the image acquisition device 1.

Next, a procedure of observing the X-ray transmission image of the target object F using the image acquisition device 1 according to the present embodiment, that is, a flow of the radiographic image processing method according to the present embodiment will be described. FIG. 13 is a flowchart illustrating a procedure of observation processing using the image acquisition device 1.

First, the control device 20 accepts an input of condition information indicating the operating conditions of the X-ray irradiator 50, the imaging conditions of the X-ray detection camera 10, or the like from an operator (user) of the image acquisition device 1 (step S1). Next, the control device 20 calculates the value of the average energy of the X-rays detected by the X-ray detection camera 10 on the basis of the condition information (step S2).

Further, the control device 20 specifies the value of the average energy of the X-rays in the image data used to construct the trained models 206 stored in the control device 20 (step S3). Thereafter, the specification of the average energy value of the X-rays is repeated for all the trained models 206 stored in the control device 20 (step S4).

Next, the control device 20 compares the calculated average energy values of the X-rays to thereby narrow down candidates for a plurality of trained models 206 (step S5). Further, in the image acquisition device 1, a jig is set to capture an image of the jig, and thus an X-ray transmission image of the jig is acquired (step S6).

Thereafter, the control device 20 acquires the image characteristics of the X-ray transmission image of the jig (such as the average energy value of the X-rays, the characteristics of thickness-luminance, the characteristics of the luminance and a noise ratio, the characteristics of luminance-noise, and the characteristics of change in resolution) (step S7). The control device 20 then selects final trained model 206 on the basis of the acquired image characteristics (step S8).

Further, in the image acquisition device 1, the target object F is set to capture an image of the target object F, and thus an X-ray transmission image of the target object F is acquired (step S9). Next, the control device 20 applies the finally selected trained model 206 to the X-ray transmission image of the target object F, and thus the noise removal process is executed for the X-ray transmission image (step S10). Finally, the control device 20 outputs an output image which is an X-ray transmission image that has undergone the noise removal process to the display device 30 (step S11).

According to the image acquisition device 1 described above, the average energy of the X-rays passing through the target object F is calculated on the basis of the operating conditions of the source of the X-rays or the imaging conditions of the X-ray transmission image when the X-ray transmission image of the target object F is acquired. Candidates for the trained model 206 used for noise removal are narrowed down from the trained models 206 constructed in advance on the basis of the average energy. Thereby, the trained model 206 corresponding to the average energy of the X-rays which are a target for imaging is used for noise removal, and thus it is possible to realize noise removal corresponding to the relationship between luminance and noise in the X-ray transmission image. As a result, it is possible to effectively remove noise from the X-ray transmission image, and to improve, for example, foreign substance detection performance. Particularly, the mode of noise of the X-ray transmission image changes depending on differences in a tube voltage, a filter, a scintillator, conditions of an X-ray detection camera (a gain setting value, a circuit noise value, an amount of saturated charge, a conversion coefficient value (e-/count), and the line rate of the camera), a target object, and the like. For this reason, in a case where noise removal is attempted to be realized through machine learning, it is necessary to prepare a plurality of learning models trained under various conditions. In the related art, it has not been realized to select a learning model suitable for the mode of noise from a plurality of learning models in accordance with conditions during measurement of an X-ray transmission image. According to the present embodiment, the trained model 206 corresponding to the average energy of the X-rays which are a target for imaging is selected, and thus the selection of a learning model that always matches the mode of noise is realized.

Generally, an X-ray transmission image contains noise derived from the generation of X-rays. It is also conceivable to increase the X-ray dose in order to improve the SN ratio of the X-ray transmission image. However, in that case, there is a problem in that increasing the X-ray dose increases the exposure of a sensor, shortens the life of the sensor, and shortens the life of the X-ray source, and thus it is difficult to achieve both an improvement in the SN ratio and an increase in life. In the present embodiment, it is not necessary to increase the X-ray dose, and thus it is possible to achieve both an improvement in the SN ratio and an increase in life.

In addition, the control device 20 of the present embodiment has a function of executing image processing for removing noise from the X-ray transmission image of the target object F using the selected trained model 206. With such a function, it is possible to realize noise removal corresponding to the relationship between luminance and noise in the X-ray transmission image, and to effectively remove the noise in the X-ray transmission image.

In addition, the control device 20 of the present embodiment has a function of narrowing down candidates for the trained model by comparing the average energy value of the X-rays calculated from selection information with the average energy value specified from the image data used to construct the trained model 206. With such a function, it is possible to reliably realize noise removal corresponding to the relationship between luminance and noise in the X-ray transmission image.

Further, the control device 20 of the present embodiment has a function of selecting the trained model 206 from the candidates on the basis of the image characteristics of the X-ray transmission image of the jig. With such a function, it is possible to select the best trained model 206 for noise removal of the X-ray transmission image of the target object F. As a result, it is possible to more reliably realize noise removal corresponding to the relationship between luminance and noise in the X-ray transmission image.

Figure 14:
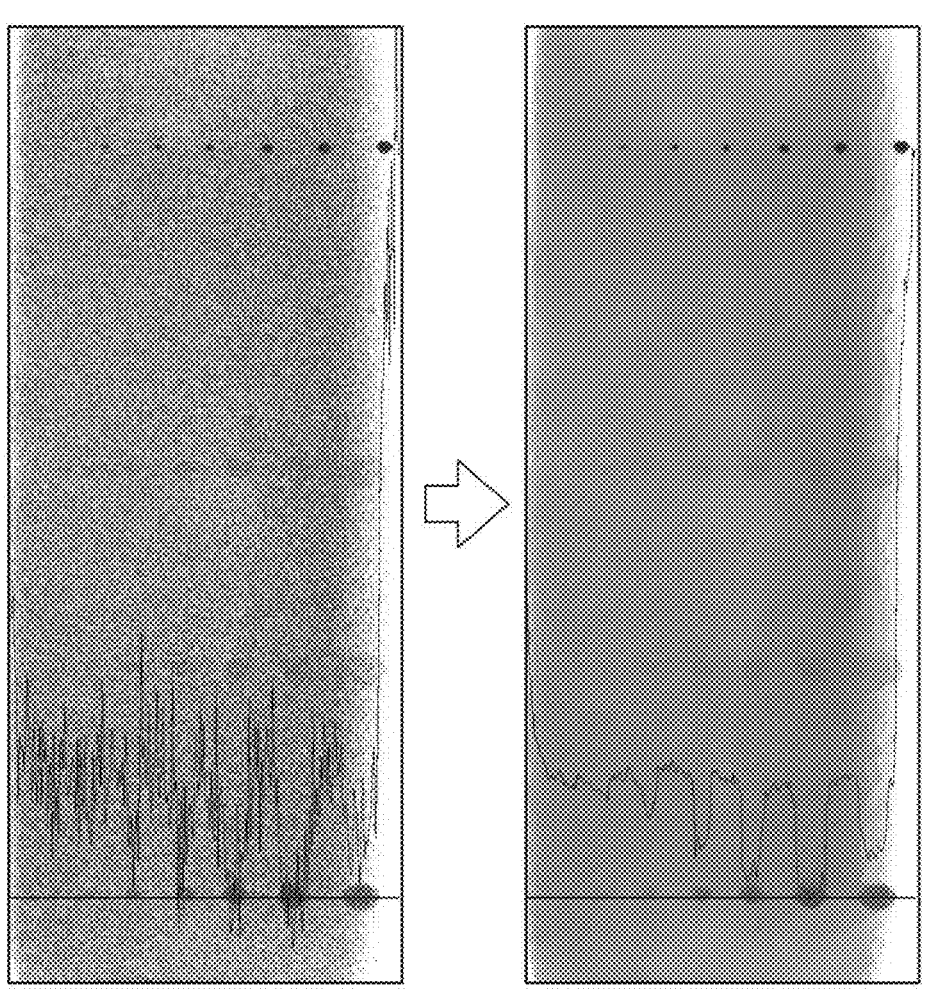
FIG. 14 is a diagram illustrating an example of an X-ray transmission image acquired by the image acquisition device 1 before and after the noise removal process.
Figure 15:
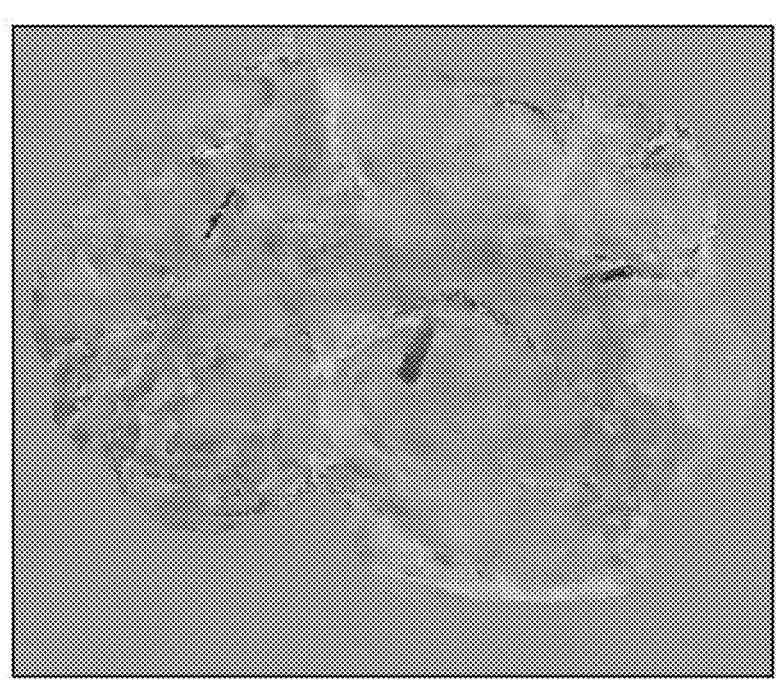
FIG. 15 is a diagram illustrating an example of an X-ray transmission image acquired by the image acquisition device 1 before and after the noise removal process.
Figure 15:
Figure 15:
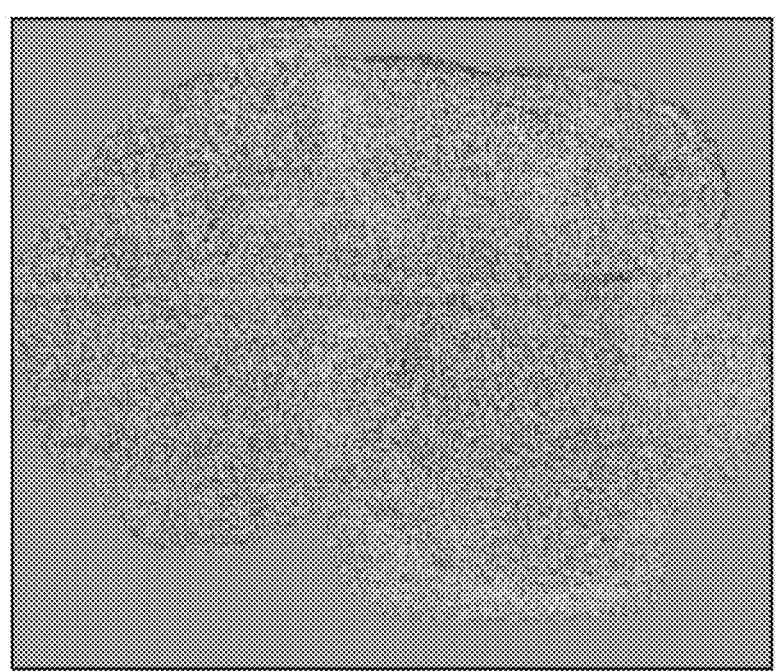

FIGS. 14 and 15 show examples of X-ray transmission images acquired by the image acquisition device 1 before and after the noise removal process. FIGS. 14 and 15 show an image of cheese to which foreign substances such as metal or glass are added and an image of chicken in which bones of various sizes remain, respectively, and show an image before noise processing on the left side and an image after noise processing on the right side, respectively. In this manner, according to the present embodiment, it can be understood that noise removal is effectively performed on various target objects.

Hereinbefore, although various embodiments of the present invention have been described, the present invention is not limited to the above embodiments, and may be modified or applied to others without changing the gist described in each claim.

For example, although the X-ray detection camera 10 has been described as a dual-line X-ray camera, the camera is not limited thereto, and may be a single line X-ray camera, a dual energy X-ray camera, a time delay integration (TDI) scan X-ray camera, a multi-line X-ray camera having a plurality of two or more lines, a two-dimensional X-ray camera, an X-rays flat panel sensor, an X-rays I.I, a direct conversion type X-ray camera (a-Se, Si, CdTe, CdZnTe, TlBr, PbI2, or the like) that does not uses a scintillator, or an observation type camera using an optical lens with a scintillator based on lens coupling. In addition, the X-ray detection camera 10 may be a camera tube sensitive to radiation or a point sensor sensitive to radiation.

In addition, the control device 20 of the above embodiment has selected candidates for the trained model 206 on the basis of the average energy value of the X-rays calculated from the condition information, but it may have a function corresponding to a degradation in performance of the X-ray detection camera 10 and a fluctuation in output of the X-ray irradiator 50 or a degradation in performance thereof as in a control device 20A according to a modification example shown below.

In addition, the image acquisition device 1 is not also limited to the above embodiment, and may be a radiographic image processing system such as a computed tomography (CT) device that captured an image of the target object F in a stationary state. Further, the image acquisition device may be a radiographic image processing system that captures an image of the target object F while rotating the target object.

Figure 16:
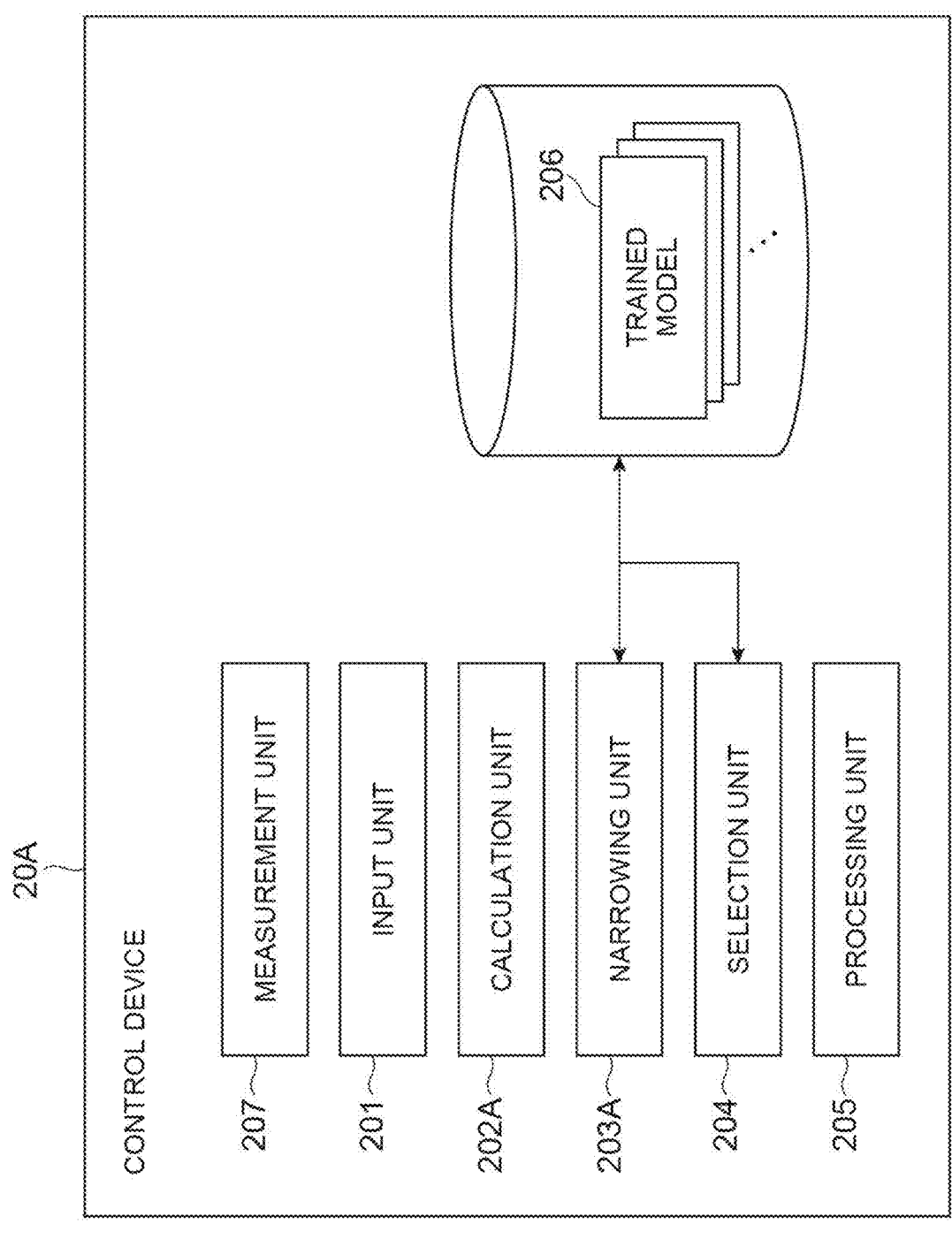
FIG. 16 is a block diagram illustrating a functional configuration of a control device 20A according to a modification example of the present disclosure.

FIG. 16 is a block diagram illustrating a functional configuration of the control device 20A according to a modification example. The control device 20A is different from the control device 20 according to the above embodiment in that it has a measurement unit 207 and has different functions of a calculation unit 202A and a narrowing unit 203A.

The control device 20 has no degradation in performance of the X-ray detection camera 10 and no fluctuation in output of the X-ray irradiator 50 or no degradation in performance thereof, and narrows down the trained models 206 on the premise that the relationship between luminance and noise in the X-ray transmission image can be estimated from the average energy of the X-rays. On the other hand, the control device 20A according to the present modification example has a function of calculating an X-ray conversion coefficient in consideration of a degradation in performance of the X-ray detection camera 10 and a fluctuation in output of the X-ray irradiator 50 or a degradation in performance thereof, and narrowing down the trained models 206 on the basis of the X-ray conversion coefficient. The X-ray conversion coefficient is a parameter indicating the efficiency until the X-rays are converted into visible light by a scintillator and then converted into electrons (electrical signal) by a camera sensor.

Generally, when the average energy of the X-rays is E [keV], the light emission amount of the scintillator is EM [photon/keV], the coupling efficiency in the sensor is C, and the quantum efficiency of the sensor is QE, the X-ray conversion coefficient $F_T$ can be calculated using the following expression.

$$F_T = E \times EM \times C \times QE$$

In addition, the SN ratio (SNR) in the X-ray transmission image is obtained from the following expression using the X-ray conversion coefficient $F_T$, the X-rays photon number $N_P$, and the readout noise Nr of the camera.

$$SNR = F_T N_P / \{(F_T N_P + Nr^2)^{1/2}\}$$

Thus, the relationship between luminance and noise in the X-ray transmission image after considering a degradation in performance of the camera can be estimated on the basis of the X-ray conversion coefficient $F_T$.

The measurement unit 207 of the control device 20A has a function of measuring the amount of decrease in the light emission amount EM as a degradation in performance of the scintillators 11a and 11b, the amount of decrease in the quantum efficiency QE of the sensor as a degradation in performance of the line scan cameras 12a and 12b, and the amount of change in the average energy E as a fluctuation in output of the X-ray irradiator 50 and a degradation in performance thereof. For example, the measurement unit 207 measures the amount of decrease in the light emission amount between a state where there is no degradation in performance of the scintillators 11a and 11b (state when new) and the current scintillators 11a and 11b, and estimates the current light emission amount EM from the amount of decrease. In addition, the measurement unit 207 measures the amount of decrease in luminance between a state where there is no degradation in performance of the line scan cameras 12a and 12b (state when new) and the current line scan cameras 12a and 12b, and estimates the current quantum efficiency QE from the amount of decrease. In addition, the measurement unit 207 estimates the current average energy E from the amount of change in the average energy between a state where there is no degradation in performance of the X-ray irradiator 50 (state when new) and the current X-ray irradiator 50. The average energy E may be obtained from imaging data of a flat plate-like member whose thickness and material are known and in which a relationship between the average energy of the X-rays and the transmittance of the X-rays is known, may be obtained from imaging data at a plurality of points of the jig whose thickness or material changes, or the like.

The calculation unit 202A of the control device 20A calculates the X-ray conversion coefficient $F_T$ using the calculated average energy E of the X-rays and the light emission amount EM and quantum efficiency QE estimated by the measurement unit 207. The narrowing unit 203 of the control device 20A has a function of narrowing down candidates for the trained model 206 by comparing the calculated X-ray conversion coefficient $F_T$ with the X-ray conversion coefficient $F_T$ in the image data used to construct the trained model 206.

Figure 17:
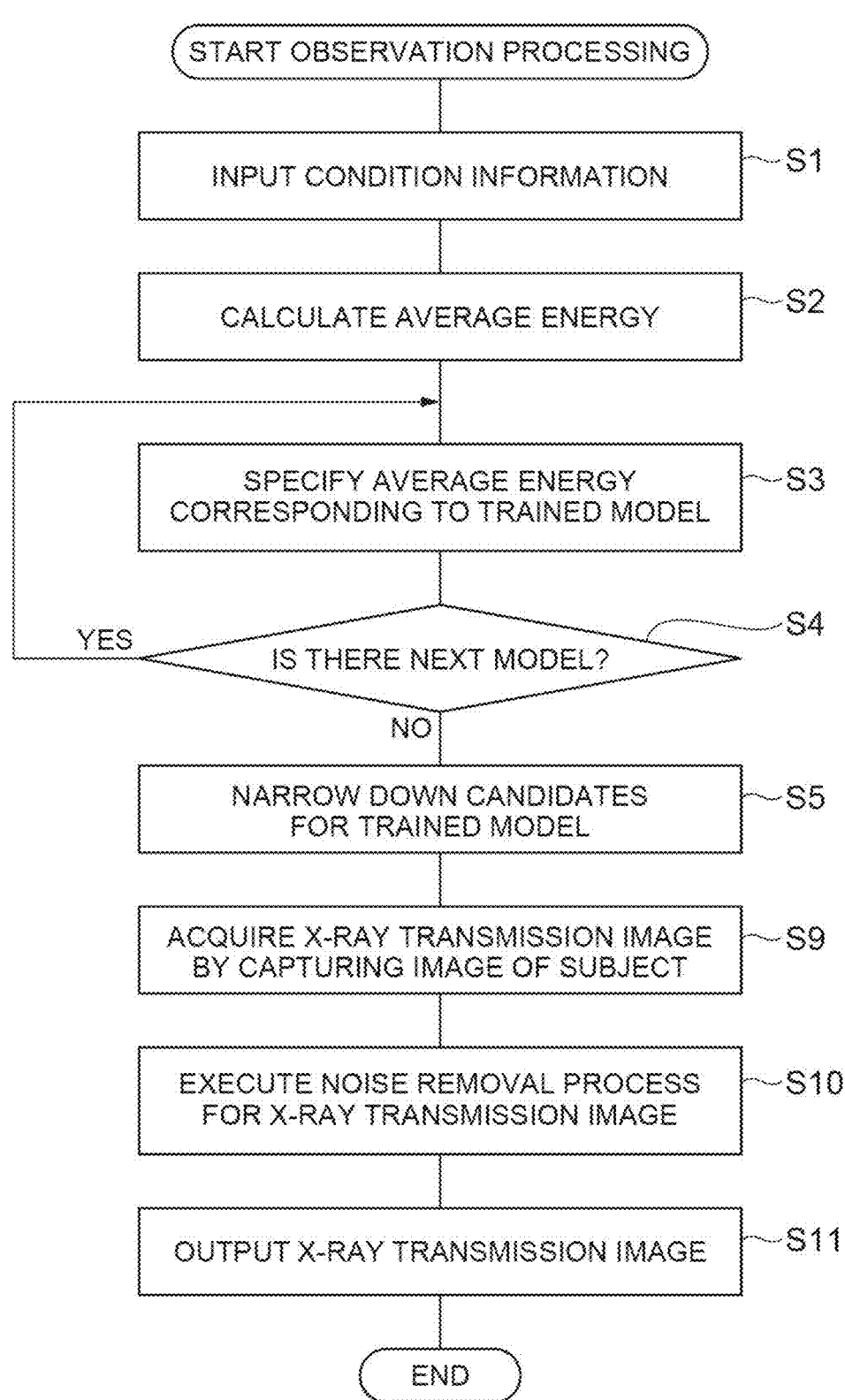
FIG. 17 is a flowchart illustrating a procedure of observation processing using the image acquisition device 1 according to the modification example.

In addition, the control device 20 of the above embodiment narrows down candidates for the trained model and then selects the trained model on the basis of the image characteristics obtained by capturing an image of the jig, but it may execute the noise removal process with respect to the X-ray transmission image of the target object without capturing an image of the jig. FIG. 17 is a flowchart illustrating a procedure of observation processing using the image acquisition device 1 according to the modification example. In this way, it is also possible to omit the processes of the steps S6 to S8 in FIG. 13 and to execute the noise removal process using the trained models narrowed down on the basis of the average energy.

In the above-described embodiment, it is preferable to further include a step of executing image processing for removing noise from a radiographic image of the target object using the candidates. In the above embodiment, it is preferable to further include a processing unit configured to execute image processing for removing noise from a radiographic image of the target object using the candidates. Thereby, it is possible to realize noise removal corresponding to a relationship between luminance and noise in a radiographic image, and to effectively remove noise from the radiographic image.

In addition, it is also preferable that the step of narrowing down includes narrowing down the candidates by comparing the average energy with average energy specified from the image data. In addition, it is also preferable that the narrowing unit narrows down the candidates by comparing the average energy with average energy specified from the image data. In this case, the trained models are narrowed down by comparison with the average energy specified from the image data used to construct the trained model, and thus it is possible to reliably realize noise removal corresponding to the relationship between luminance and noise in the radiographic image.

Further, it is preferable that the condition information includes at least any one of a tube voltage of the source, information on a filter included in a camera used to capture an image of the target object, information on a filter included in the source, information on a scintillator included in the camera, a distance between the source and an imaging device, information relating to an X-ray detection camera used to capture an image of the target object, and information relating to the target object. In this case, the average energy of the radiation passing through the target object can be calculated accurately, and thus it is possible to perform noise removal corresponding to the relationship between luminance and noise in the radiographic image.

In addition, it is preferable to further include a step of acquiring a radiographic image by radiating the radiation to capture an image of a jig and selecting a trained model from the candidates on the basis of image characteristics of the radiographic image. In addition, it is preferable to further include a selection unit configured to acquire a radiographic image by radiating the radiation to capture an image of a jig and select a trained model from the candidates on the basis of image characteristics of the radiographic image. With such a configuration, the trained model is selected on the basis of the image characteristics of the radiographic image obtained by capturing an image of an actual jig, and thus it is possible to select the best trained model for noise removal of the radiographic image of the target object. As a result, it is possible to more reliably realize noise removal corresponding to the relationship between luminance and noise in the radiographic image.

The embodiment uses a radiographic image processing method, a trained model, a radiographic image processing module, a radiographic image processing program, and a radiographic image processing system, thereby allowing noise in a radiographic image to be effectively removed.

REFERENCE SIGNS LIST

10 X-ray detection camera (imaging device)
20 Control device (radiographic image processing module)
201 Input unit
202, 202A Calculation unit
203, 203A Narrowing unit
204 Selection unit
205 Processing unit
206 Trained model
F Target object

The invention claimed is:

1. A radiographic image processing method comprising:
   inputting condition information indicating either conditions of a source of radiation or imaging conditions when the radiation is radiated to capture an image of a target object;
   calculating average energy related to the radiation passing through the target object on the basis of the condition information;
   narrowing down candidates for a trained model from a plurality of trained models constructed through machine training in advance using image data on the basis of the average energy; and
   executing image processing for removing noise from a radiographic image of the target object using the candidates.

2. The radiographic image processing method according to claim 1, wherein narrowing down includes narrowing down the candidates by comparing the average energy with average energy specified from the image data.

3. The radiographic image processing method according to claim 1, wherein the condition information includes at least any one of a tube voltage of the source, information on a filter included in a camera used to capture an image of the target object, information on a filter included in the source, information on a scintillator included in the camera, a distance between the source and an imaging device, information relating to an X-ray detection camera used to capture an image of the target object, and information relating to the target object.

4. The radiographic image processing method according to claim 1, further comprising acquiring a radiographic image by radiating the radiation to capture an image of a jig and selecting a trained model from the candidates on the basis of image characteristics of the radiographic image.

5. The radiographic image processing method according to claim 1, wherein the machine training is deep learning.

6. A trained model used for the radiographic image processing method according to claim 1, wherein the trained model is constructed through machine training using image data and causes a processor to execute image processing for removing noise from a radiographic image of the target object.

7. A radiographic image processing module comprising:
   at least one processor,
   wherein the at least one processor is configured to
   accept an input of condition information indicating either conditions of a source of radiation or imaging conditions when the radiation is radiated to capture an image of a target object, calculate average energy related to the radiation passing through the target object on the basis of the condition information, narrow down candidates for a trained model from a plurality of trained models constructed through machine training in advance using image data on the basis of the average energy, and execute image processing for removing noise from a radiographic image of the target object using the candidates.

8. The radiographic image processing module according to claim 7, wherein the at least one processor narrows down the candidates by comparing the average energy with average energy specified from the image data.

9. The radiographic image processing module according to claim 7, wherein the condition information includes information relating to a tube voltage of the source, a filter, a distance between the source and an imaging device, an X-ray detection camera, and the target object.

10. The radiographic image processing module according to claim 7, wherein the at least one processor acquires a radiographic image by radiating the radiation to capture an image of a jig and selects a trained model from the candidates on the basis of image characteristics of the radiographic image.

11. The radiographic image processing module according to claim 7, wherein the machine training is deep learning.

12. A radiographic image processing program causing a processor to function as:

accepting an input of condition information indicating either conditions of a source of radiation or imaging conditions when the radiation is radiated to capture an image of a target object;

calculating average energy related to the radiation passing through the target object on the basis of the condition information;

narrowing down candidates for a trained model from a plurality of trained models constructed through machine training in advance using image data on the basis of the average energy; and executing image processing for removing noise from a radiographic image of the target object using the candidates.

13. A radiographic image processing system comprising:

the radiographic image processing module according to claim 7;

the source configured to radiate radiation to the target object; and an imaging device configured to capture an image of the radiation passing through the target object and acquire the radiographic image.

14. A machine training method comprising constructing a trained model for outputting image data from which noise has been removed on the basis of a training image using, as training data, the training image that is a radiographic image of a target object corresponding to average energy related to radiation passing through the target object, the average energy being calculated on the basis of condition information indicating either conditions of a source of the radiation or imaging conditions when the radiation is radiated to capture an image of the target object.

\* \* \* \* \*